US009192568B2

(12) United States Patent
Calvo Salve et al.

(10) Patent No.: US 9,192,568 B2
(45) Date of Patent: Nov. 24, 2015

(54) FORMULATIONS COMPRISING JORUMYCIN-, RENIERAMYCIN-, SAFRACIN- OR SAFRAMYCIN-RELATED COMPOUNDS FOR TREATING PROLIFERATIVE DISEASES

(75) Inventors: Pilar Calvo Salve, Madrid (ES); Maria Tobio Barreira, Madrid (ES)

(73) Assignee: Pharma Mar, S.A., Madrid (ES)

( * ) Notice: Subject to any disclaimer, the term of this patent is extended or adjusted under 35 U.S.C. 154(b) by 963 days.

(21) Appl. No.: 12/091,540

(22) PCT Filed: Oct. 30, 2006

(86) PCT No.: PCT/GB2006/050362
§ 371 (c)(1),
(2), (4) Date: Jun. 4, 2008

(87) PCT Pub. No.: WO2007/052076
PCT Pub. Date: May 10, 2007

(65) Prior Publication Data
US 2009/0076016 A1    Mar. 19, 2009

(30) Foreign Application Priority Data
Oct. 31, 2005    (GB) .................... 0522082.7

(51) Int. Cl.
*A61K 31/4995* (2006.01)
*A61P 35/00* (2006.01)
*A61K 9/00* (2006.01)
*A61K 9/19* (2006.01)
*A61K 47/26* (2006.01)

(52) U.S. Cl.
CPC ........... *A61K 9/0019* (2013.01); *A61K 31/4995* (2013.01); *A61K 9/19* (2013.01); *A61K 47/26* (2013.01)

(58) Field of Classification Search
CPC ... A61K 31/4995; A61K 9/0019; A61K 9/19; A61K 47/26
See application file for complete search history.

(56) References Cited

U.S. PATENT DOCUMENTS

| 5,089,273 | A | 2/1992 | Rinehart et al. |
|---|---|---|---|
| 5,149,804 | A | 9/1992 | Rinehart et al. |
| 5,213,804 | A | 5/1993 | Martin et al. |
| 5,256,663 | A | 10/1993 | Rinehart et al. |
| 5,336,669 | A | 8/1994 | Palepu et al. |
| 5,478,932 | A | 12/1995 | Rinehart et al. |
| 5,552,544 | A | 9/1996 | Bra na et al. |
| 5,654,426 | A | 8/1997 | Rinehart et al. |
| 5,721,362 | A | 2/1998 | Corey et al. |
| 5,908,835 | A | 6/1999 | Bissery |
| 5,985,876 | A | 11/1999 | Rinehart et al. |
| 6,124,293 | A | 9/2000 | Rinehart et al. |
| 6,153,590 | A | 11/2000 | Andersen et al. |
| 6,348,467 | B1 | 2/2002 | Corey |
| 7,241,892 | B1 | 7/2007 | Cuevas et al. |
| 7,247,629 | B2 | 7/2007 | Manzanares et al. |
| 7,309,601 | B2 | 12/2007 | Perez-Esteban |
| 7,410,969 | B2 | 8/2008 | Manzanares et al. |
| 7,420,051 | B2 | 9/2008 | Francesch |
| 7,524,956 | B2 | 4/2009 | Cuevas |
| 7,622,458 | B2 | 11/2009 | Rybak |
| 7,723,068 | B2 | 5/2010 | Iglesias |
| 2002/0137663 | A1 | 9/2002 | Forman et al. |
| 2002/0143038 | A1 | 10/2002 | Bandyopadhyay et al. |
| 2002/0173482 | A1 | 11/2002 | Ajani |
| 2003/0008873 | A1* | 1/2003 | Myers et al. .................. 514/249 |
| 2004/0002602 | A1 | 1/2004 | Francesch et al. |
| 2004/0019027 | A1 | 1/2004 | Forman et al. |
| 2004/0067895 | A1* | 4/2004 | Faircloth et al. ................ 514/28 |
| 2004/0108086 | A1 | 6/2004 | Takahashi et al. |
| 2005/0004018 | A1 | 1/2005 | Jimeno |
| 2006/0030571 | A1 | 2/2006 | Rinehart et al. |
| 2006/0094687 | A1* | 5/2006 | Beijnen et al. .................. 514/53 |
| 2007/0004691 | A1 | 1/2007 | Donald et al. |
| 2007/0082856 | A1 | 4/2007 | Gianni et al. |
| 2007/0128201 | A1 | 6/2007 | D'Incalci et al. |
| 2007/0275942 | A1 | 11/2007 | Cvitkovich |
| 2008/0076772 | A1 | 3/2008 | Allavena |
| 2008/0255132 | A1 | 10/2008 | Rowinsky |
| 2008/0293725 | A1 | 11/2008 | Rosell Costa |
| 2009/0117176 | A1 | 5/2009 | Gilles |
| 2009/0170860 | A1 | 7/2009 | Scotto |
| 2009/0324744 | A1 | 12/2009 | Takahashi |
| 2010/0009906 | A1 | 1/2010 | Ali Elsayed |

FOREIGN PATENT DOCUMENTS

| CN | 1486193 | 3/2004 |
|---|---|---|
| JP | 5-501264 | 3/1993 |
| JP | 2000081438 | 3/2000 |

(Continued)

OTHER PUBLICATIONS

Akers ('Excipient—Drug Interactions in Parenteral Formulations') in Journal of Pharmaceutical Sciences 9(11), 2283-2300 (2002).*
Van Kesteren et al. in Anti-Cancer Drugs 2003, 14:487-502.*
Akers, M.J. in Journal of Pharmaceutical Sciences 9(11), 2283-2300 (2002).*
Elices et al. in 96th Annual Meeting of the American Association for Cancer research, Abstract #623, Apr. 17, 2005.*
Martinez et al. in PNAS USA 96, 3496-3501 (1999).*
Blay et al., "Phase I Combination Study of Trabectedin and Doxorubicin in Patients with Soft-Tissue Sarcoma," Clin. Cancer Res., 2008, 14(20), 6656-6662.
Chu et al., "Phase I and Pharmacokinetic Study of Sequential Paclitaxel and Trabectedin Every 2 Weeks in Patients with Advance Solid Tumors," Clin. Cancer Res., 2008, 16(9), 2656-2665.
Gore et al., "Phase I Combination Study of Trabectedin (T) and Capecitabine (C) in Patients With Advanced Malignancies," Journal of Clinical Oncology, 2006 ASCO Annual Meeting Proceedings, vol. 24, No. 18S (Jun. 20 Supplement), 2006: Abstract 2079.

(Continued)

*Primary Examiner* — Dennis Heyer
(74) *Attorney, Agent, or Firm* — Kenneth H. Sonnenfeld; Bryte V. Kelly; King & Spalding LLP

(57) ABSTRACT

Jorumycin, renieramycin, safracin and saframycin related compounds formulations, methods of preparing the same, articles of manufacture and kits with such formulations, and methods of treating proliferative diseases with the same formulations are provided.

39 Claims, 1 Drawing Sheet

(56) References Cited

FOREIGN PATENT DOCUMENTS

| | | | | |
|---|---|---|---|---|
| WO | WO 91/05546 | 5/1991 | | |
| WO | WO 98/52598 | 11/1998 | | |
| WO | WO 99/51238 | 10/1999 | | |
| WO | WO 99/58125 | 11/1999 | | |
| WO | WO 00/69441 | * 11/2000 | ........... | A61K 31/495 |
| WO | WO 00/69862 | 11/2000 | | |
| WO | WO 01/77115 | 10/2001 | | |
| WO | WO 01/87894 | * 11/2001 | ........... | C07D 515/22 |
| WO | WO 02/36135 | 5/2002 | | |
| WO | WO 02/064843 | * 8/2002 | ................ | C12R 1/00 |
| WO | WO 02/078678 | 10/2002 | | |
| WO | WO 03/020259 | 3/2003 | | |
| WO | WO 03/039571 | 5/2003 | | |
| WO | WO 2005/049029 | 6/2005 | | |
| WO | WO 2005/049030 | 6/2005 | | |
| WO | WO 2005/049031 | 6/2005 | | |
| WO | WO 2005/118584 | 12/2005 | | |
| WO | WO 2006/035244 | 4/2006 | | |
| WO | WO 2006/046080 | 5/2006 | | |
| WO | WO 2006/066183 | 6/2006 | | |

OTHER PUBLICATIONS

Grasselli et al., "Phase I and Pharmacokinetic (PK) Study of Ecteinascidin-743 (ET, Trabectedin) and Cisplatin (P) Combination in Pre-Treated Patients (PTS) With Selected Advanced Solid Tumors," Abstract 542 of 39$^{th}$ Annual Meeting of American Society of Clinical Oncology (ASCO), May 31-Jun. 3, 2003.
Messersmith et al., "Phase I Trial of Weekly Trabectedin (ET-743) and Gemcitabine in Patients with Advanced Solid Tumors," Cancer Chemother Pharmacol, 2008, 63, 181-188.
Salazar et al., "Clinical and Pharmacokinetic Phase I Combination Study of Trabectedin (T) and Carboplatin (C) in Patients with Advanced Solid Tumors," Abstract 424P of 31$^{st}$ ESMO (European Society for Medical Oncology) Congress, Sep. 29-Oct. 3, 2006.
Von Mehren et al., "Phase I Study of Trabectedin (T) in Combination with Docetaxel (D) in Patients with Advanced Malignancies," Journal of Clinical Oncology, 2006 ASCO Annual Meeting Proceedings, vol. 24, No. 18S (Jun. 20 Supplement), 2006: Abstract 2068.
Von Mehren et al., "A Phase I Study of the Safety and Pharmacokinetics of Trabectedin in Combination with Pegylated Liposomal Doxorubicin in Patients with Advanced Malignancies," Annals of Oncology, 2008, 19, 1802-1809.
U.S. Appl. No. 09/546,877, filed Apr. 10, 2000, Rinehart.
U.S. Appl. No. 09/787,461, filed Mar. 2, 2001, Cvitkovich.
U.S. Appl. No. 10/257,856, filed Mar. 31, 2003, Andres Francesch.
U.S. Appl. No. 10/416,086, filed Sep. 17, 2003, Takahashi.
U.S. Appl. No. 10/492,320, filed Oct. 21, 2002, Jimeno.
U.S. Appl. No. 10/558,133, filed Nov. 15, 2006, D'Incalci.
U.S. Appl. No. 10/575,132, filed Oct. 14, 2004, Donald.
U.S. Appl. No. 10/579,130, filed May 12, 2006, Rowinsky.
U.S. Appl. No. 10/579,251, filed Oct. 20, 2006, Gianni.
U.S. Appl. No. 11/132,466, filed May 18, 2005, Rinehart.
U.S. Appl. No. 11/261,876, filed Oct. 28, 2005, Beijnen.
U.S. Appl. No. 11/571,589, filed Jan. 3, 2007, Rosell-Costa.
U.S. Appl. No. 11/576,115, filed Sep. 28, 2005, Allavena.
U.S. Appl. No. 11/577,790, filed Apr. 23, 2007, Gilles.
U.S. Appl. No. 11/769,873, filed Jun. 28, 2007, Cvitkovich.
U.S. Appl. No. 12/094,744, filed Nov. 17, 2008, Kathleen Scotto.
U.S. Appl. No. 12/299,960, filed Mar. 23, 2009, Yusri Ali Elsayed.
U.S. Appl. No. 12/552,347, filed Sep. 2, 2009, Naoto Takahashi.
Aboussekhra, A. et al. "Mammalian DNA Nucleotide Excision Repair Reconstituted with Purified Protein Components" Cell 1995, 80, 859-868.
Akers, "Excipient-Drug Interactions in Parenteral Formulations," Journal of Pharmaceutical Sciences, 91(11), pp. 2283-2300, Nov. 2002.
Alexopoulos, "Phase II study of pegylated liposomal doxorubicin (Caelyx(R)) and docetaxel as first-line treatment in metastatic breast cancer," Ann. Oncol., 2004, 15(6):891-5.
Barrera, H. et al., "Interaction of ET-743 and standard cytotoxic agents against a panel of human tumor cell lines," Proceedings of the American Association for Cancer Research, vol. 40, p. 591, Abstract No. 3896, Mar. 1999.
Biroccio et al., "Telomere Dysfunction Increases Cisplatin and Ecteinascidin-743 Sensitivity of Melanoma Cells," Molecular Pharmacology, 63:632-638 (2003).
Blay et al., "Combination of Trabectedin and Doxorubicin for the Treatment of Patients with Soft Tissue Sarcoma: Safety and Efficacy Analysis," 43rd annual ASCO meeting, Jun. 1-5, 2007.
Bonfanti et al., "Effect ofEcteinascidin-743 on the Interaction Between DNA Binding Proteins and DNA." Anticancer Drug Des. 14, 179-86, 1999.
Bootsma, D. et al. The Genetic Basis of Human Cancer, 1$^{st}$ ed.; Vogelstein B, Kinzler KW Eds.; McGraw Hill: Toronto, 1998; pp. 245-274.
Boranic et al., "A Parkinson-like Syndrome as Side Effect of Chemotherapy with Vincristine and Adriamycin in a Child With Acute Leukeamia," Biomedicine, vol. 31(5), pp. 124-5, 1979.
Brandon et al., In-vitro Cytotoxicity of ET-743 (Trabectedin, Yondelis), a Marine Anti-cancer Drug, in the Hep G2 Cell Line: Influence of Cytochrome P450 and Phase II Inhibition, and Cytochrome P450 Induction, Anti-cancer Drugs, 16:935-943 (2005).
Bowman, A. et al., "Phase I clinical and pharmacokinetic (PK) study of ecteinascidin-743 (ET-743) given as a one hour infusion every 21 days," Annals Oncology, Abstract 452, 1998.
Bueren, J. A. et al. Generation of DNA double strand breaks Turing trabectedin DNA damage measured trough induction of γH2AX [abstract]. In: American Association for Cancer Research Annual Meeting: Proceedings; Apr. 14-18, 2007; Los Angeles, CA. Philadelphia (PA): AACR; 2007. Abstract nr 1965; and the corresponding poster presented in said congress.
Burstein et al., "Phase I study of Doxil and Vinorelbine in Metastatic Breast Cancer," Annals of Oncology, vol. 10, pp. 1113-1116, 1999, XP8086751.
Campos, Susana "Liposomal anthracyclines: Adjuvant and Neoadjuvant Therapy for breast cancer," The Oncologist 2003:8 (suppl. 2): 10-16.
Caponigro, F. et al., "Phase I study of Caelyx (doxorubicin HCI, pegylated liposomal) in recurrent or metastatic head and neck cancer," Annals of Oncology, vol. 11, pp. 399-342, 2000.
Carboplatin: Summary of Product Characteristics, Hospira UK Ltd., available from the internet at <<http://emc.medicines.org.uk>>, pp. 1-10, last modified Jan. 29, 2009.
Casali et al., "Activity of Ecteinascidin-743 (ET-trabectedin) 3-hour Infusion in Adult and Childhood Small Round Cell Sarcomas," ASCO Annual Meeting, 2003, Abstract 962.
Chabner et al., Cancer Chemotherapy and Biotherapy: Principles and Practice, Third Edition, pp. 1-16, 2001.
Chabner, "Cytotoxic agents in the era of molecular targets and genomics," The Oncologist, vol. 7, suppl. 3, pp. 34-41, 2002.
Chinese J. New Drugs Clin. Rem., 2001, pp. 216, 219.
Committee on Risk Assessment Methodology, "Issues in Risk Assessment. Appendix A: Workshop Summary-Maximum Tolerated Dose: Implications for Risk Assessment," National Research Council, National Academy of Sciences, National Academies Press, Washington DC, pp. 79-89, 1993.
Corey et al., "Enantioselective Total Synthesis of Ecteinascidin 743", J. Am. Chem. Soc., 118, 9202-9203, 1996.
Cvetkovic et al., "ET-743," Drugs, vol. 62(8), pp. 1185-1192, 2002.
Cvitkovic, E. et al., "Final results of a phase I study of ecteinascidin-743 (ET-743) 24 hour (h) continuous infusion (CI) in advanced solid tumors (AST) patients (pts)," 1999 ASCO Annual Meeting Proceedings, Abstract No. 690, May 15-18, 1999.
Cvitkovic, E. et al., "Ecteinascidin-743 (ET-743) 24 hour continuous intravenous infusion (CI) phase I study in solid tumors (ST) patients," Annals Oncology, Abstract 456, 1998.
Damia, G. et al. ET743-Induced changes in gene expression in murine cells defective in nucleotide excision repair [abstract]. In: AACR-NCI-EORTC International Conference on Molecular Targets and Cancer Therapeutics; Oct. 22-Nov. 2, 2001; Miami, US. Philadelphia (PA): ACCR, 2001. Abstract No. 666.

(56) References Cited

OTHER PUBLICATIONS

Delaloge et al., "Ecteinascidin (ET-743) in heavily pretreated refractory sarcomas: Preliminary evidence of activity," Eur. J. Cancer, vol. 35, suppl. 4, p. S271, Abstract No. 1080, Sep. 15, 1999.

Delaloge, S. et al., "Ecteinascidin-743: A Marine-Derived Compound in Advanced Pretreated Sarcoma Patients-Preliminary Evidence of Activity", J. of Clinical Oncology, vol. 19, No. 5, pp. 1248-1255, 2001.

DeVita et al., "Combination Versus Single Agent Chemotherapy: A Review of the Basis for Selection of Drug Treatment of Cancer", Cancer, vol. 35, pp. 98-110, 1975.

D'Incalci et al., "Mode of action of Ecteinascidin-743 (ET-743)," Proceedings of the 1999 AACR-NCI-EORTC International Conference, Clinical Cancer Research, vol. 5, Supplement, pp. 3872s-3873s, Abstract of Plenary Session 7, Nov. 16-19, 1999.

D'Incalci et al., "The Combination of ET-743 and Cisplatin (DDP): From a Molecular Pharmacology Study to a Phase I Clinical Trial," from the AACR Annual Meeting of Apr. 6-10, 2002, Abstract 404.

D'Incalci et al., "In human tumor xenografts the resistance to ET-743 or to cisplatin can be overcome by giving the two drugs in combination," European Journal of Cancer, 38, Suppl. 7, 34 (Nov. 2002).

D'Incalci et al., "Preclinical and Clinical Results with the Natural Marine Product ET-743," Expert Opin. Investig. Drugs, 12(11):1843-1853 (2003).

D'Incalci et al., "The combination of yondelis and cisplatin is synergistic against human tumor xenografts," European Journal of Cancer 39: 1920-1926 (2003).

D'Incalci et al., "Unique Features of the Mode of Action of ET-743", The Oncologist, 7, p. 210-216, Jun. 2002.

Donald et al, "Comparison of four modulators of drug metabolism as protectants against the hepatotoxicity of the novel antitumor drug yondelis (ET-743) in the female rat and in hepatocytes in vitro," Cancer Chemother Pharmacol, Apr. 2004, vol. 53, pp. 305-12.

Donald et al., "Complete Protection by High-Dose Dexamethasone Against The Hepatotoxicity of the Novel Antitumor Drug Yondelis (ET-743) in The Rat," Cancer Research, vol. 63, p. 5902-5908, Sep. 2003.

Donald et al., "Dietary Agent Indole-3-Carbinol Protects Female Rats Against the Hepatotoxicity of the Antitumor Drug ET-743 (trabectidin) Without Compromising Efficacy in a Rat Mammary Carcinoma" International Journal of Cancer, vol. 111, No. 6, p. 961-967, 2004.

Dorr and Van Hoff, "Doxorubicin," Cancer Chemotherapy Handbook, 1994, pp. 395-416.

"Doxil (doxorubicin HCI Liposome Injection) Product Information", Oct. 10, 2004, pp. 1-16, XP002389462, <<web.archive.org/web/20041009180>>.

Drugs Fut., "Ecteinascidin-743" vol. 22, No. 11, p. 1279, 1997.

Eckhardt et al., "In vitro Studies of a Novel Marine Cytotoxic, Ecteinascidin (ET-743)," New Drugs and Pharmacology, Annals of Oncology, 7 (Suppl. 5), 131, Abstract 632P (1996).

Endo et al., "Total Synthesis of Ecteinascidin 743", J. Am. Chem. Soc., 124, 6552-6554, 2002.

Erba, E. et al. "Ecteinascidin-743 (ET-743), a natural marine compound, with a unique mechanism of action" Eur. J. Cancer 2001, 37, 97-105.

Erba et al., "Synergistic cytotoxic effect of ET-743 and cisplatin," Clinical Cancer Research, vol. 6, Abstract 209, Nov. 7-10, 2000.

Erba et al., "Combination of yondelis (ET-743) and oxaliplatin in experimental ovarian cancer," from the AACR-NCI-EORTC International Conference on Molecular Targets and Cancer Therapeutics of Nov. 17-21, 2003, Abstract C247.

Erba et al., "ET-743 and Cisplatin (DDP) Show in Vitro and in Vivo Synergy Against Human Sarcoma and Ovarian Carcinoma Cell Lines," from the AACR-NCI-EORTC Conference on Molecular Targets and Cancer Therapeutics of Oct. 29-Nov. 2, 2001, Abstract 406.

Erlichman, C., "18: Pharmacology of Anticancer Drugs,"The Basic Science of Oncology, 2nd edition, Tannock et al., editors, McGraw-Hill, New York, pp. 317-337, 1992.

European Agency for the Evaluation of Medicinal Products, "Committee for Proprietary Medicinal Products Summary of Opinion for Yondelis", Nov. 20, 2003.

European Medicines Agency (EMEA), "Scientific Discussion" from the European Public Assessment Report for Yondelis®, Revision 1, published Mar. 31, 2008, downloaded from the internet on Apr. 2, 2008, from the website <<http://www.emea.europa.eu/humandocs/Humans/EPAR/yondelis/yondelis.htm>>.

FDA approved label for Pharmacia and Upjohn's Doxorubicin Hydrochloride for Injection (May 8, 2003).

Faircloth et al., "In Vivo Combinations of Chemotherapeutic Agents with Ecteinascidin 743 (ET743) Against Solid Tumors," from the Proceedings AACR-NCI-EORTC of Nov. 2001, Abstract 387.

Faircloth et al., "Dexamethasone Potentiates the Activity of Ecteinascidin 743 in Preclinical Melanoma and Osteosarcoma Models," Abstract and Presentation 379 (2002).

Faulkner et al., "Symbiotic Bacteria in Sponges: Sources of Bioactive Substances," Drugs from the Sea, Fusetani, N. (ed.), Basel Karger, 2000, pp. 107-119.

Fayette et al., "ET-743: a Novel Agent with Activity in Soft-Tissue Sarcomas," Current Opinion in Oncology, 18:347-353 (2006).

Fourouzesh, B. et al., "Phase I and pharmacokinetic study of the marine-derived DNA minor groove binder ET-743 on a weekly x3 every-4-week schedule in patients with advanced solid malignancies," Proceedings of the 2001 AACR-NCI-EOTRC International Conference, Abstract No. 209, Oct. 29-Nov. 2, 2001.

Fourouzesh, B. et al., "Phase I and pharmacokinetic study of ET-743, a minor groove DNA binder, administrated weekly to patients with advanced cancer," Proc Am Soc Clin Oncol, vol. 20, 2001 ASCO Annual Meeting Proceedings, Abstract No. 373, 2001.

Forouzesh, B., et al., "Phase I and pharmacokinetic study of ET-743, a minor groove DNA binder, administered weekly to patients with advanced cancer," European Journal of Cancer, EECO 11, vol. 37, supplement 6, Abstract No. 106, Oct. 21-25, 2001.

Forouzesh et al., Proc. Am. Soc. Clin. Oncol. ASCO meeting, Abstract 373, Jun. 3, 2001, Internet Archive Entry from the website <<http://web.archive.org/web/*/http://www.asco.org/>>, 32 pages.

Friereich et al., "Quantitative Comparison of Toxicity of Anticancer Agents in Mouse, Rat, Hamster, Dog, Monkey, and Man," Cancer Chemotherapy Reports, 50:4, May 1966, pp. 219-245.

Fukuyama et al., "Total Synthesis of Saframycin A," J. Am. Chem. Soc., 112, 3712-3713, 1990.

Fukuyama et al., "Stereocontrolled Total Synthesis of Saframycin B," J. Am. Chem. Soc., 104, 4957-4958, 1982.

Gabizon et al., "Pharmacokinetics of Pegylated Liposomal Doxorubicin," Clin. Pharmacokinet 2003:42(5), pp. 419-436.

Garcia-Carbonero et al., "Population pharmacokinetics of ecteinascidin 743 in patients with advanced soft tissue sarcoma," Clinical Cancer Research, vol. 6, Supplement, Abstract 211, p. 4508s, NCI-EORTC-AACR Symposium on New Drugs in Cancer Therapy, Nov. 7-10, 2000.

Garcia Gravalos, M.D., et al., "In vitro schedule-dependent cytotoxicity by ecteinascidin 743 (ET-743) against human tumor cells," 23rd European Society for Medical Oncology Congress, Abstract No. 652, Nov. 6-10, 1998.

Ghielmini, M. et al., "Schedule-dependent myelotoxicity induced in vitro by the new marine derived minor groove interacting agent ecteinascidin 743," ECCO, vol. 9, Abstract No. 807, Sep. 17, 1997.

Ghielmini, M. et al., "In vitro schedule-dependency of myelotoxicity and cytotoxicity of Ecteinascidin 743 (ET-743)," Annals of Oncology, vol. 9, pp. 989-993, 1998.

Gianni et al. "Definition of the Least Toxic Sequence and Optimal Therapeutic Dose of Yondelis® in Combination with Doxorubicin in Patients with Untreated Metastatic Soft Tissue Sarcomas and Advanced Pre-Treated Anthracycline," Clinical Cancer Research, vol. 9, No. 16, p. 6081S (Dec. 2003).

Giovanna et al., "Importance of DNA repair mechanisms for the sensitivity of tumor cells to ET-743," Proceedings of the 1999 AACR-NCI-EORTC International Conference, Clinical Cancer Research, vol. 5, Supplement, p. 3790s, Abstract 303, Nov. 16-19, 1999.

Gogas et al., "Neoadjuvant Chemotherapy with a Combination of Pegylated Liposomal Doxorubicin (Caelyx®) and Paclitaxel in

(56) References Cited

OTHER PUBLICATIONS

Locally Advanced Breast Cancer: A Phase II Study by the Hellenic Cooperative Oncology Group," Annals of Oncology, pp. 1737-1742, 2002.
Goodman & Gilman's The Pharmaceutical Basis of Therapeutics, p. 36, 1975.
Goodman & Gilman's The Pharmaceutical Basis of Therapeutics (9$^{th}$ edition), p. 930, 1996.
Goodman & Gilman's The Pharmaceutical Basis of Therapeutics (9$^{th}$ edition), pp. 1230-1232, 1996.
Gore et al., "Phase I Combination Study of Trabectedin and Capecitabine in Patients With Advanced Malignancies," Poster Presentation, 42nd ASCO Annual Meeting held on Jun. 2-6, 2006, Atlanta, Georgia.
Gourley C. et al., "Malignant mixed Mesodermal Tumours—Biology and Clinical Aspects," European Journal of Cancer, 2002, vol. 38, No. 11, pp. 1437-1446.
Grazziotin Soares, D. et al., "Low cytotoxicity of ecteinascidin 743 in yeast lacking the major endonucleolytic enzymes of base and nucleotide excision repair pathways" Biochemical Pharmacology 2005, 70, 59-69.
Grazziotin Soares, D. et al., "Replicationn and homologous recombination repair regulate DNA double-strand break formation by the antitumor alkylator ecteinascidin 743" PNAS 2007, 104, 13062-13067.
Greyer et al., "The National Cancer Institute: Cancer Drug Discovery and Development Program", Seminars in Oncology, vol. 19, No. 6, 622-638, Dec. 1992.
Grosso et al., "Steroid Premedication Markedly Reduces Liver and Bone Marrow Toxicity of Trabectedin in Advanced Sarcoma," European Journal of Cancer 42:10, 1484-1490 (2006).
Grosso, F. et al., Trabectedin (T) in soft tissue sarcomas (STS) carrying a chromosomal translocation: An exploratory analysis [abstract]. In: 13$^{th}$ CTOS Annual Meeting; Nov. 1-3, 2007; Seattle, WA. p. 51. Abstract nr 900; and the corresponding oral presentation presented en said congress.
Gurtler, J.S. et al., "Trabectedin in third line breast cancer: a multicenter, randomized, phase II study comparing two administration regimens," Journal of Clinical Oncology, 2005 ASCO Annual Meeting Proceedings, vol. 23, No. 16S, part I of II (Jun. 1 Supplement), Abstract No. 625, 2005.
Hahn et al., "Taxol in Combination with Doxorubicin or Etoposide," Cancer, vol. 72, No. 9, pp. 2705-2711, Nov. 1, 1993.
Halm et al., "A phase II study of pegylated liposomal doxorubicin for treatment of advanced hepatocellular carcinoma," Ann. Oncol., 2000, 11(1):113-114.
Hendriks, H.R. et al., "High antitumor activity of ET743 against human tumor xenografts from melanoma, non-small-cell lung and ovarian cancer," Annals of Oncology, vol. 10, pp. 1233-1240, 1999.
Herrero, A. B. et al. "Cross-Talk between Nucleotide Excision and Homologous Recombination DNA Repair Pathways in the Mechanism of Action of Antitumor Trabectedin" Cancer Res., 2006, 66, 8155-8162.
Hidalgo, M., et al., "A phase I and pharmacokinetic (PK) study of ET-743, a novel minor groove binder of marine origin administered on a daily x 5 schedule," 23rd European Society for Medical Oncology Congress, Abstract No. 613P, Nov. 6-10, 1998.
Hillebrand, M.J.X. et al., "Pharmacokinetics of ecteinascidin-743 (ET-743) in three phase I studies," Annals Oncology, Abstract No. 455, 1998.
Hoekman at al., "A phase I/II study of dose-escalated docetaxel given two weekly in combination with a fixed dose of G-CSF," European Journal of Cancer, vol. 37, p. S76, Abstract 270, Oct. 22, 2001.
Holmes, "Paclitaxel Combination Therapy in the treatment of Metast Breast Cancer: A Review," Seminars in Oncology, vol. 23, pp. 46-56, 1996.
Hornicek et al., "In vitro effect of the tetrahydroisoquinoline alkaloid Ecteinascidin-743 (ET-743) on chondrosarcoma (CHSA) cells," Proceedings of the 1999 AACR-NCI-EORTC International Conference, Clinical Cancer Research, vol. 5, Supplement, p. 3790s, Abstract 304, Nov. 16-19, 1999.
Hornicek et al., "Effect of Ecteinascidin-743 and Plasminogen related Protein B on a Human Chondrosarcoma Xenograft Tumor in Mice," Clinical Cancer Research, vol. 7 Supplement P3734S-3734S, Abstract 398 (Nov. 2001).
Horstmann et al., "Risks and Benefits of Phase I Oncology Trials, 1991 through 2002," New England Journal of Medicine, vol. 352, pp. 895-904; Mar. 3, 2005.
Hosomi et al., "Phase I Study of Cisplatin and Docetaxel Plus Mitomycin C in Patients with Metastatic Non-Small Cell Lung Cancer," Jpn. J. Clin. Oncol., 29(11), pp. 546-549, 1999.
Hussein et al., "A Phase II Trial of Pegylated Liposomal Doxorubicin, Vincristine, and Reduced-Dose Dexamethasone Combination Therapy in Newly Diagnosed Multiple Myeloma Patients," Cancer, Nov. 15, 2002, vol. 95, No. 10, pp. 2160-2168.
Ilson et al., "A Phase II Trial of Paclitaxel and Cisplatin in Patients with Advanced Carcinoma of the Esophagu," Cancer J, 6(5), 316-23, 2000.
Ishikawa et al., "Tumor Selective Delivery of 5-Fluorouracil by Capecitabine," Biochemical Pharmacology, vol. 55, pp. 1091-1097, 1998.
Italiano, A. et al. ERCC5 (XPG) status and clinical activity of trabectedin in patients with advanced soft-tissue sarcoma [abstract]. In: Proceedings of the 101$^{th}$ Annual Meeting of the American Association for Cancer Research; Apr. 17-21, 2010; Washington, DC. Philadelphia (PA): AACR; 2010. Abstract No. 2699; and the corresponding poster presented in said congress.
Izbicka, E. et al., "In vitro antitumor activity of the novel marine agent, Ecteinascidin-743 (ET-743, NSC- 648766) against human tumors explanted from patients." Annals of Oncology, vol. 9, pp. 981-987, 1998.
Jimeno, J.M. et al., "Enhancing the preclinical in vivo antitumor activity of ecteinascidin 743, a marine natural product currently in phase II clinical trials," Proceedings of the 1999 AACR-NCI-EORTC International Conference, Clinical Cancer Research, vol. 5, p. 3790S, Abstract No. 306, Nov. 16-19, 1999.
Jimeno et al., "Pharmacokinetics (PK)/Pharmacodynamic (PD) Relationships in Patients (PT) Treated With Ecteinascidin-743 (ET-743) Given as 24 Hours Continuous Infusion (CI)," Journal of Clinical Oncology, ASCO Annual Meeting Proceedings, Abstract No. 744, May 15-18, 1999.
Jimeno, J. et al., "Phase I and pharmacokinetic (PK) study of ET-743, a novel minor groove binder of marine origin on a daily [times] 5 schedule," 1998 ASCO Annual Meeting Proceedings, Abstract No. 737, 1998.
Jimeno, Jose et al., "Adding Pharmacogenomics to the Development of New Marine-Derived Anticancer Agents," Journal of Translational Medicine, vol. 4, issue 3, Jan. 9, 2006, downloaded from the internet website: <<http://www.translational-medicine.com/content/4/1/3>>.
Jin et al., "The antitumor agent Ecteinascidin 743 (ET743), inhibits transcriptional activation of the MDR1 Gene by multiple inducers," Proceedings of the 1999 AACR-NCI-EORTC International Conference, Clinical Cancer Research, vol. 5, Supplement, p. 3790s, Abstract 302, Nov. 16-19, 1999.
Jin et al., Ecteinascidin-743, A Transcription-Targeted Chemotherapeutic that Inhibits MDR I Activation. Proc. Natl. Acad. Sci. USA, 97, 6775-9, 2000.
Kanzaki et al., "Activity of Ecteinascidin 743 and Synergism with Doxorubicin and Vincristine in P-Glycoprotein/MDR1 Over-Expression Cell Lines," from the Proceedings of the AACR, vol. 42, Abstract 4354 (Mar. 2001).
Kanzaki et al., "Microsatellite Instability (MSI) Induced by Ecteinascidin743 and Protection with Aspirin," from the 93rd Annual Meeting of the American Association for Cancer Research, Abstract 5382 (Apr. 6-10, 2002), vol. 43, Mar. 2002, p. 1087.
Kesteren Ch. Van et al., "Yondelis® (trabectedin, ET-743): the development of an anticéncer agent of marine origin" Anti-Cancer Drugs, 2003, 14, 487-502.
Kononen, J. et al., "Tissue microarrays for high-throughput molecular profiling of tumor specimens" Nature Med., 1998, 4, 844-847.

(56) References Cited

OTHER PUBLICATIONS

Kovalcik et al., "The Stability of Cyclophosphamide in Lyophilized Cakes. part I. Mannitol, Lactose, and Sodium Biocarbonate as Excipients," Journal of Parenteral Science and Technology, vol. 42, No. 1, Jan.-Feb. 1988, pp. 29-37.
Kraemer, K. H. et al., "The Role of Sunlight and DNA Repair in Melanoma and Nonmelanoma Skin Cancer. The Xeroderma Pigmentosum Paradigm" Arch. Dermatol., 1994, 130, 1018-1021.
Kraemer, K. H. et al. "Xeroderma Pigmentosum. Cutaneous, Ocular, and Neurologic Abnormalities in 830 Published Cases" Arch. Dermatol., 1987, 123, 241-250.
Krafft, A. E. et al., "Optimization of the Isolation and Amplification of RNA From Formalin-fixed, Paraffin-embedded Tissue: The Armed Forces Institute of Pathology Experience and Literature Review" Mol. Diagn., 1997, 2, 217-230.
Laverdiere et al., "Phase II Study of Ecteinascidin 743 in Heavily Pretreated Patients with Recurrent Osteosarcoma", Cancer, American Cancer Society, Philadelphia, PA, Aug. 15, 2003, vol. 98:4, pp. 832-840, XP002314512.
Lau et al., "A Phase I and Pharmacokinetic Study of Ecteinascidin-743 (Yondelis) in Children with Refractory Solid Tumors." Clinical Cancer Research, vol. 11, pp. 672-677, Jan. 15, 2005.
Le Morvan, V. et al., Genetic polymorphisms of the XPG and XPD nucleotide excision repair genes in sarcoma patients [abstract]. In: Proceedings of the 96$^{th}$ Annual Meeting of the American Association for Cancer Research; Apr. 16-20, 2005; Anaheim/Orange County, CA. Philadelphia (PA): AACR; 2005. Abstract No. 4099.
Le Morvan, V. et al. "Genetic polymorphisms of the XPG and XPD nucleotide excision repair genes in sarcoma patients," Int. J. Cancer, 2006, 119, 1732-1735.
Le Page, F. et al., "Transcription-Coupled Repair of 8-oxoGuanine: Requierement for XPG, TFIIH, and CSB and Implications for Cockayne Syndrome," Cell 2000, 101, 159-171.
Leonetti et al., "Antitumoral Effect of the G-quadraplex Interactive Compound RHPS4 on Human Melanoma Cells Possessing Relatively Long Telomeres," from the Proceedings of the AACR, vol. 45, Mar. 2004.
Lopez-Lazaro et al., "Exploratory evaluation of the potential predictors for dose-limiting toxicities (DLTs) in patients treated with Ecteinascidin-743 (ET-743) as a 24-h intravenous (iv) infusion every 3 weeks and its relationship to pharmacokinetics (PK)," Proceedings of the 1999 AACR-NCI-EORTC International Conference, Clinical Cancer Research, vol. 5, Supplement, p. 3791s, Abstract 308, Nov. 16-19, 1999.
Lu, Wan-Liang et al., "A pegylated liposomal platform: pharmacokinetics, pharmacodynamics, and toxicity in mice using doxorubicin as a model drug," J of Pharmacological Sciences, 95, 381-389, 2004.
Lyass et al., "Phase I Study of Doxil-Cisplatin Combination Chemotherapy in Patients with Advanced Malignancies," Clinical Cancer Research, vol. 7, pp. 3040-3046, Oct. 2001, XP8086753.
Maier et al., "In vitro inhibition of endothelial cell growth by the antiangiogenic drug AGM-1470 (TNP-470) and the antiendoglin antibody TEC-11," Anti-Cancer Drugs, vol. 8, pp. 238-244, 1997.
Magro et al., "The Role of PARP and PARP Inhibitors in Yondelis (Trabectedin) Mediated Cytotoxicity," Abstract and Presentation from the AACR Annual Meeting, Apr. 17, 2007.
Manzanares et al., "Advances in the Chemistry and Pharmacology of Ecteinascidins, A Promising New Class of Anticancer Agents," Curr. Med. Chem—Anti-Cancer Agents, 2001, vol. 1, pp. 257-276.
Martinez et al., "Phthalascidin, A Synthetic Antitumor Agent with Potency and Mode of Action Comparable to Eeteinaseidin 743." Proc. Natl. Acad. Sci. USA 96; 3496-501, 1999.
Martinez, E. J. et al., "A New, More Efficient, and Effective Process for the Synthesis of a Key Pentacyclic Intermediate for Production of Ecteinascidin and Phthalascidin Antitumor Agents." Org. Lett. 2, 993-6, 2000.
Martinez, N. et al., "Transcriptional signature of Ecteinascidin 743 (Yondelis, Trabectedin) in human sarcoma cells explantes from chemo-naive patients," Mol. Cancer Ther., 2005, 4, 814-823.
McLeod, "Clinically relevant drug-drug interactions in oncology," Br. J. Clin. Pharmacol., 45:539-544 (1998).
McMeekin, D.S. et al., "Final results of a phase II study of weekly trabectedin in second/third line ovarian carcinoma," Journal of Clinical Oncology, 2005 ASCO Annual Meeting Proceedings, vol. 23, No. 16S, Part I of II (Jun. 1 Supplement), Abstract No. 5011, May 13-17, 2005.
McMeekin et al., "Trabectedin (T) in Relapsed Advanced Ovarian Cancer (ROC): A Pooled Analysis of Three Phase II Studies," Journal of Clinical Oncology, 25(18S), Abstract No. 5579, 2007 ASCO Annual Meeting.
Meco et al., "Effective combination of ET-743 and doxorubicin in sarcoma: preclinical studies," Cancer Chemother. Pharmacol. 52: 131-138 (2003).
Meco et al., "The combination of ET-743 and Irinotecan is active in preclinical models in rhabomyosarcoma," presented at the 16th EORTC-NCI-AARC Symposium on Molecular Targets and Cancer Therapeutics held in Geneva on Sep. 28-Oct. 1, 2004.
Menchaca et al., "Synthesis of Natural Ecteinascidins (ET-729, ET-745, ET-759B, ET-736, ET-637, ET-594) from Cyanosafracin B," J. Org. Chem., published on web Oct. 21, 2003, pp. 8859-8866.
Merck Manual on-line edition version, "Types: Overview of Cancer," 4 pages, downloaded from internet website <<http://www.merck.com/mmhe>>, Feb. 2003.
Michaelson, M.D. et al., "Phase II study of three hour, weekly infusion of trabectedin (ET-743) in men with metastatic, androgen-independent prostate carcinoma (AIPC)," Journal of Clinical Oncology, 2005 ASCO Annual Meeting Proceedings, vol. 23, No. 16S, Part I of II (Jun. 1 Supplement), Abstract No. 4517, May 13-17, 2005.
Minuzzo, M. et al., "Interference of Transcriptional Activation by the Antineoplastic Drug Ecteinascidin.743." Proc. Natl. Acad. Sci. USA 97, 6780-4, 2000.
Moneo, V. et al., "Extreme Sensitivity to Yondelis® (Trabectedin, ET-743) in Low Passaged Sarcoma Cell Lines Correlates With Mutated p53," J. Cell. Biochem., 2007, 100, 339-348.
Monk et al., "A Randomized Phase III Study of Trabectedin With Pegylated Liposmal Doxorubicin (PLD) Versus PLD in Relapsed, Recurrent Ovarian Cancer (OC)," Annals of Oncology, 19(8), 2008.
Moore et al., "Sequencing evaluation of ET-743 combinations with standard chemotherapy agents against a panel of human tumor cell lines," Clinical Cancer Research, vol. 6, Abstract 504 (Nov. 2000).
Morioka et al., "Antiangiogenesis Treatment Combined with Chemotherapy Produces Chondrosarcoma Necrosis," Clinical Cancer Research, vol. 9, 1211-1217, Mar. 2003.
Mu, D. et al., "Reaction Mechanism of Human DNA Repair Excision Nuclease," J. Biol. Chem., 1996, 271, 8285-8294.
Mudgett. J. S. et al., "Isolation of the Functional Human Excision Repair Gene ERCC5 by Intercosomid Recombination," Genomics 1990, 8, 623-633.
Newell et al., "The Cancer Research UK experience of pre-clinical toxicology studies to support early clinical trials with novel cancer therapies," European Journal of Cancer, v. 40, pp. 899-906, 2004.
Nouspikel, T. et al., "Mutations that disable the DNA repair gene XPG in a xeroderma pigmentosum group G patient," Hum. Mol. Genet., 1994, 3, 963-967.
O'Brien et al., "Reduced Cardiotoxicity and Comparable Efficacy in a Phase III Trial of Pegylated Liposomal Doxorubicin HCI (CAELYX™/Doxil®) Versus Conventional Doxorubicin for First-Line Treatment of Metastatic Breast Cancer," Annals of Oncology, vol. 15, pp. 440-449, 2004.
O'Donovan, A. et al., "Identical defects in DNA repair in xeroderma pigmentosum group G and rodent ERCC group 5," Nature, 1993, 363, 185-188.
Pasetto et al., "Improved Tolerability of Chemotherapy in Soft Tissue Sarcomas: Old and New Strategies," Expt. Rev. Antican. Ther., vol. 3(2), pp. 167-178, 2003.
Perotti et al., "Cardiotoxic effects of anthracylcine-taxane combinations," Expert Opin Drug Saf, 2(1), 59-71, Jan. 2003.
Pharma Mar Press Release, "PharmaMar Differs with CPMP Opinion", Pharma Mar Grupo Zeltia, << http://www.pharmamarcom/en/press/news_release.cfm>>, Jul. 24, 2003.

(56) References Cited

OTHER PUBLICATIONS

Pharma Mar Press Release, "PharmaMar Receives EMEA Appeal Decision on Yondelis in Soft Tissue Sarcoma", Pharma Mar Grupo Zeltia, <<http://www.pharmamar.com/en/press/news_release.cfm>>, Nov. 20, 2003.

Pharma Mar Press Release, "YONDELIS(r) STS-201 Efficacy and Safety Data Presented at ASCO 2007" Pharma Mar Grupo Zeltia, <<http://www.pharmamar.com/en/press>>, Jun. 5, 2007.

Pharma Mar Press Release, "The European Commission Authorizes YONDELIS(r) Commericalization for Soft Tissue Sarcoma" Pharma Mar Grupo Zeltia, <<http://www.pharmamar.com/en/press>>, Sep. 20, 2007.

Pommier et al., "DNA Sequence- and Structure-Selective Alkylation of Guanine N2 in the DNA Minor Groove by Ecteinascidin 743, a Potent Antitut:11or Compound from the Caribbean Tunicate *Ecteinascidia turbinata*." Biochemistry 35, 13303-9, 1996.

Pourquier, P. et al., "Nucleotide excision repair-mediated cytotoxicity of ecteinascidin 743, a novel anticancer agent in clinical trials," In: Proceedings of the 92$^{nd}$ Annual Meeting of American Association for Cancer Research; Mar. 24-28, 2001; New Orleans, LA, USA. Philadelphia (PA): AACR; 2001. p. 556. Abstract No. 2987.

PR Newswire, PR Newswire, Oct. 14, 2001, 4 pages.

Puchalski et al., "Pharmacokinetics of Ecteinascidin 743 Administered as a 24-h Continuous Intravenous Infusion to Adult Patients with Soft Tissue Sarcomas associations with Clinical Characteristics, Pathophysiological Variables and Toxicity," Cancer Chemotherapy and Pharmacology, 2002, vol. 50, No. 4, pp. 309-319.

Rinehart, K.L., "Antitumor Compounds from Tunicates." Med. Res. Rev. 20, 127, 2000.

Riccardi et al., "Preclinical Activity and Biodistribution of Ecteinascidin 743 (ET-743) and Doxorubicin (DOX) Combinations in Human Rhabdomyosarcoma," from the AACR-NCI-EORTC Conference on Molecular Targets and Cancer Therapeutics of Oct. 29-Nov. 2, 2001, Abstract 405.

Riccardi et al., "Effective Combinations of ET-743 and Doxorubicin for Tumor Growth Inhibitions Against Murine and Human Sarcomas in Athymic Mice," from the Proceedings of the AACR, vol. 42, Abstract 1132 (Mar. 2001).

Riccardi et al., "Combination of trabectedin and irinotecan is highly effective in a human rhabdomyosarcoma xenograft," Anti-Cancer Drugs, 16:811-815 (2005).

Riofrio, M. et al., "Ecteinascidin-743 (ET-743) 24 hours continuous infusion (CI): Clinical and pharmacokinetic phase I study progressive report," 23rd European Society for Medical Oncology Congress, Abstract 639 P, Nov. 6-10, 1998.

Rimassa et al., "Unexpected Low Efficacy of Stealth Liposomal Doxorubicin (Caelyx) and Vinorelbine in Metastatic Breast Cancer," Breast Cancer Research and Treatment, 77, 2003, pp. 185-188.

Rivera, Engardo "Liposomal anthracyclines in metastatic breast cancer: Clinical Update," The Oncologist, 2003:8 (suppl. 2):3-9.

Robert et al.,"Pharmacokinetics of Doxorubicin in Sarcoma Patients," Eur. J. Clin. Pharmocol., vol. 31, pp. 695-699, 1987.

Rose et al., "A Phase I Trial of Prolonged Oral Etoposide and Liposomal Doxorubicin in Ovarian, Peritoneal, and Tubal Carcinoma: A Gynecologic Oncology Group Study," Gynecologic Oncology, 85, 2002, pp. 136-139.

Rosell, R. et al., "Expression of XPG mRNA and protein as potential biomarker of response to trabectedin in sarcoma patients," In: AACR-NCI-EORTC International Conference on Molecular Targets and Cancer Therapeutics; Oct. 22-26, 2007; San Francisco, CA. Philadelphia (PA): AACR, 2007, Abstract No. C127; and the corresponding poster presented in said congress.

Rosell, R. et al., "DNA repair efficiency as a model for personalizaed therapy with Trabectedin," In: AACR Molecular Diagnostic in Cancer Therapeutic Development; Sep. 17-20, 2007; Atlanta, GA. Philadelphia (PA): AACR; 2007. p. 44. Abstract No. A57; and the corresponding poster presented in said congress.

Rosing et al., "Pharmacokinetics (PK) of Ecteinascidin-743 (ET-743) in three different phase I trials," Proceedings of the American Association for Cancer Research, vol. 40, pp. 81, abstract No. 542, Mar. 1999.

Rote Liste 2002 "Doxorubicin," entries 86-056 through 86-062, 2002.

Ryan, D.P. "Studies with Ecteinascidin-743 (ET-743) A Marine Alkaloid," Cancer Invest, vol. 18 (suppl 1), pp. 112, abstract No. 87, Jan. 2000, from the Chemotherapy Foundation Symposium XVII Innovative Cancer Therapy for Tomorrow, Nov. 3-6, 1999, New York, NY.

Ryan, DP et al., "Phase I and Pharmacokinetic Study of Ecteinascidin-743 Administered as a 72 hours Continuous Intravenous Infusion in Patients with Solid Malignancies", Clinical Cancer Research, vol. 7, pp. 231-242, 2001.

Safra, Tamar "Cardiac safety of liposomal anthracyclines," The Oncologist 2003:8 (suppl. 2): 17-24.

Saito et al.,"Synthesis of Saframycins-3," J. Org. Chem., 54, 5391, 1989.

Sakai et al., "Additional Antitumor Ecteinascidins from a Caribbean Tunicate: Crystal Structures and Activities in vivo," Proc. Natl. Acad. Sci., vol. 89, Dec. 1992, pp. 11456-11460.

Sarosy et al., "Phase I Study of α2-interferon plus Doxorubicin in Patients with Solid Tumors," Cancer Research, vol. 46, pp. 5368-5371, 1986.

Sato et al., "Multicenter Phase II Trial of Weekly Paclitazel for Advanced or Metastatic Breast Cancer: the Saitama Breast Cancer Clincal Study Group (SBSSCG-01)," Japanese Journal of Clinical Oncology, Vo. 33, No. 8, pp. 371-376, Aug. 2003.

Schöffski, P. et al., "DNA repair functionality as a molecular signature for sensitivity(S)/resistance(R) in sarcoma patients (pts) treated with trabectedin (ET-743, Yondelis®)," In: American Association for Cancer Research Annual Meeting: Proceedings; Apr. 14-18, 2007; Los Angeles, CA. Philadelphia (PA): AACR; 2007. Abstract No. 144; and the corresponding poster presented in said congress.

Schwartsmann G. et al., "Marine Organisms as a Source of New Anticancer Agents," The Lancet Oncology, 2001, vol. 2, No. 4, pp. 221-225.

Scotlandi et al., "Effectiveness of Ecteinascidin-743 against Drug-sensitive and —resistant Bone Tumor Cells," Clinical Cancer Research, 8:3893-3903, 2002.

Scotto et al., "Ecteinascidin 743, a novel chemotherapeutic agent that targets transcriptional activation of a subset of genes, including MDR1," Clinical Cancer Research, vol. 6, Supplement, Abstract 210, pp. 4508s, NCI-EORTC-AACR Symposium on New Drugs in Cancer Therapy, Nov. 7-10, 2000.

Sessa et al., "Trabectedin for Women with Ovarian Carcinoma After Treatment with Platinum and Taxane Fails," Journal of Clinical Oncology, vol. 23, No. 9, pp. 1867-1874, Mar. 20, 2005.

Shertzer et al., "Protection Against Carbon Tetrachloride Hepatoxicity by Pretreatment with indole-3-carbinol," Exptl. Molec. Pathol., vol. 46, pp. 180-189 (1987).

Shertzer et al., "Protection from N-Nitrosodimethylamine Mediated Liver Damage by Indole-3-carbinol," Exptl. Molec. Pathol., vol. 47, pp. 211-218, 1987.

Shimizu et al., "Phase I Study of Docetaxel and Cyclophosphamide in Patients with Advanced or Recurrent Breast Cancer," Breast Cancer, 10(2), pp. 140-148, Apr. 2003.

Slamon et al., "Use of chemotherapy plus a monoclonal antibody against HER2 for metastatic breast cancer that overexpresses HER2", New England Journal of Medicine, 2001, 344(11):783-92.

Smyth, "Rationale for Drug Combinations," European Journal of Cancer, 39, 1816-1817 (2003).

Sparano et al., "Phase I Trial of Pegylated Liposomal Doxorubicin and Docetaxel in Advanced Breast Cancer," J. Clinical Oncology, vol. 19(12), pp. 3117-3125, 2001.

Specht, K. et al., "Quantitative Gene Expression Analysis in Microdissected Archival Formalin-Fixed and Paraffin-Embedded Tumor Tissue," Am. J. Pathol. 2001, 158, 419-429.

Stevens, E. et al., "Ecteinascidin-743 (Et-743) and Transcription-Coupled Nucleotide Excision Repair (TC-NER): Translational and Clinical Study in Ovarian Cancer," In: Proceedings of the 94$^{th}$ Annual

(56) References Cited

OTHER PUBLICATIONS

Meeting of the American Association for Cancer Research; Jul. 11-14, 2003; Washington, DC. Philadelphia (PA): AACR; 2003. Abstract No. 468.

Stevens, E. V. et al., "Predicting cisplatin and trabectedin drug sensitivity in ovarian and colon cancers," Mol. Cancer Ther., 2008, 7, 10-18.

Taamma et al., "Ecteinascidin-743 (ET-743) 24 hour continuous intravenous infusion (CI) phase I study in solid tumors (ST) patients (pts)." Proceedings of the American Association for Cancer Research, vol. 39, pp. 323, abstract No. 2207, Mar. 1998.

Taamma, A. et al., "Ecteinascidin-743 (ET-743) 24 hours continuous infusion (CI): clinical and pharmacokinetic phase I study in solid tumor patients (PTS). Preliminary Results" 1998 ASCO Annual Meeting Proceedings, Abstract No. 890, 1998.

Taamma et al., "Ecteinascidin-743 (ET-743) in heavily pretreated refractory sarcomas: early results of the French experience," Proceedings of the 1999 AACR-NCI-EORTC International Conference, Clinical Cancer Research, vol. 5, Supplement, p. 3791s, Abstract 309, Nov. 16-19, 1999.

Taamma et al., "Phase I and Pharmcokinetic Study of Ecteinascidin-743, a New Marine Compound, Administered as a 24 hours Continuous Infusion in Patients with Solid Tumors", J. of Clinical Oncology, vol. 19, No. 5, pp. 1256-1265, Mar. 1, 2001.

Taamma et al., "Phase I Clinical Study of ecteinascidin-743 (ET-743) as a 24 hours continuous intravenous infusion (CI) in patients (pts) with solid tumors (st): A progress report," Eur. J. Cancer, 33 Suppl. 8, S247-S248, Abstract, 1997.

Taamma, A. et al., "Phase I clinical study of ecteinascidin-743 (ET-743) as a 24 hours continuous intravenous infusion (CI) in patients (pts) with solid tumors (st): A progress report," ECCO, vol. 9, Abstract No. 1119, Sep. 18, 1997.

Tabor et al., "Anti oxidation Potential of Indole Compounds-Structure Activity Studies," Biological Reactive Intermediates IV, p. 833-836, 1990.

Takebayashi, Y. et al., "Antiproliferative activity of ecteinascidin 743 is dependent upon transcription-coupled nucleotide-excision repair," Nature Med., 2001, 7, 961-966.

Takebayashi, Y., "Loss of heterozygosity of nucleotide excision repair factors in sporadic ovarian, colon and lung carcinomas: implications for their roles of carcinogenesis in human solid tumors," Cancer Lett. 2001, 174, 115-125.

Takebayashi, Y. et al., "Nucleotide excision repair (XPG)-dependent antiproliferative activity of ecteinascidin 743," In: Proceedings of the $92^{nd}$ Annual Meeting of the American Association for Cancer Research; Mar. 24-28, 2001; New Orleans, LA, USA. Philadelphia (PA): AACR; 2001. p. 813. Abstract No. 4365.

Takebayashi et al., "Poisoning of Human DNA Topoisomerase I by Ecteinascidin 743, An Anticancer Drug That Selectively Alkylates DNA in the Minor Groove." Proc. Natl. Acad. Sci. USA 96, 7196-201 1999.

Takebayashi et al., "Multidrug Resistance Induced by DNA Minor Groove Alkylation of Ecteinascidin 743 (ET743)," Proceedings of the 1999 AACR-NCI-EORTC International Conference, Clinical Cancer Research, vol. 5, Supplement, p. 3851s, Abstract 602, Nov. 16-19, 1999.

Takebayashi et al., "Nucleotide excision repair-dependent cytotoxicity of Ecteinascidin 743," Clinical Cancer Research, vol. 6, Supplement, Abstract 207, p. 4508s, NCI-EORTC-AACR Symposium on New Drugs in Cancer Therapy, Nov. 7-10, 2000.

Takahashi et al., "Ecteinascidin 743 (ET-743) and doxorubicin produce synergistic cytotoxic effects in soft tissue sarcoma lines HT-1080 and HS-18," Clinical Cancer Research, vol. 6, Abstract 208, Nov. 7-10, 2000.

Takahashi et al., "Sequence-dependent Enhancement of Cytotoxicity Produced by Ecteinascidin 743 (ET-743) with Doxorubicin or Paclitaxel in Soft Tissue Sarcoma Cells," Clinical Cancer Research, 7: 3251-3257 (Oct. 2001).

Takahashi et al., "Sequence-dependent Synergistic Cytotoxicity of Ecteinascidin-743 and Paclitaxel in Human Breast Cancer Cell Lines in Vitro and in Vivo," Cancer Research, 62: 6909-6915 (Dec. 1, 2002).

Taron, M. et al., "BRCA1 expression and customized chemotherapy," In: Eurocancer. XX Congrès; Jun. 26-28, 2007; Paris. Paris: John Libbey Eurotext, 2007. pp. 107-108.

Ten Hagen et al., "Pegylated Liposomal Tumor Necrosis Factor-Alpha Results in Reduced Toxicity and Synergistic Antitumor Activity after Systemic Administration in Combination with Liposomal Doxorubicin (Doxil) in soft tissue Sarcoma-Bearing Rats," Int. J. Cancer, vol. 97, pp. 115-120, 2002.

Tercero, J. C. et al., "Predicting sarcoma patients response to trabectedin treatment with molecular markers detected by inmunohistochemistry," In: AACR International Conference: Molecular Diagnostics in Cancer Therapeutic Development; Sep. 22-25, 2008; Philadelphia, PA. Philadelphia (PA): AACR, 2008. p. 44. Abstract nr B8; and the corresponding poster presented in said congress; and the corresponding poster presented in said congress.

Twelves, C.J. et al., "Phase I clinical and pharmacokinetic (PK) study of ecteinascidin-743 (ET-743) given as a one hour infusion every 21 days," 1998 ASCO Annual Meeting Proceedings, Abstract No. 889, 1998.

Twelves, C.J. et al., "Phase I and pharmacokinetic study of ecteinascidin-743 (ET-743) given as a one hour infusion every 21 days," ECCO, vol. 9, Abstract No. 1107, Sep. 18, 1997.

Twelves et al., "A Phase I and Pharmacokinetic (PK) study of Et-743 evaluating a 3 hours (h) intravenous (iv) infusion (I) in patients (pts) with solid tumors," Clinical Cancer Research, Abstract #307, 5 (11, suppl. 3790S-3791S), Nov. 16-19, 1999.

Twelves et al., "Phase I Trials with ET-743, a marine derived (MD) anticancer agent," Eur. J. Cancer, vol. 35, suppl. 4, p. S283, Abstract No. 1135, Sep. 15, 1999.

Twelves et al., "Phase I and pharmacokinetic study of YondelisTM (Ecteinascidin-743; ET-743) administered as an infusion over 1 h or 3 h every 21 days in patients with solid tumours," European Journal of Cancer, vol. 39, p. 1842-1851, 2003; available online Aug. 14, 2003.

United States Pharmacopeia/National Formulary, "2010 USP/NF: The Official Compendia of Standards," United States Pharmacopeial Convention, $28^{th}$ Edition, vol. 1, 2009, p. 1441-1446.

Uziely et al., "Liposomal doxorubicin: antitumor activity and unique toxicities during two complementary phase I studies," Journal of Clinical Oncology, Jul. 1, 1995, vol. 13, No. 7, pp. 1777-1785.

Valoti, G., et al., "Ecteinascidin-743 (ET-743), a marine natural compound, shows antitumor activity against human ovarian carcinoma xenografts," European Journal of Cancer (Novel Therapeutics and Pharmacology), vol. 34, Supp. 2, p. S39, Abstract PP179, 1998.

Valoti, G. "Ecteinascidin-743, a New Marine Natural Product with Potent Antitumor Activity on Human Ovarian Carcinoma Xenografts," Clin. Cancer Res., vol. 4, pp. 1977-83, Aug. 1998.

van Kesteren et al., "Pharmacokinetics and Pharmacodynamics of the Novel Marine-derived Anticancer Agent Ecteinascidin 743 in a Phase I Dose-finding Study," Clinical Cancer Research, vol. 6, pp. 4725-2732, Dec. 2000.

van Kesteren et al. "Clinical Pharmacology of the Novel Marine-derived Anticancer Agent Ecteinascidin 743 Administered as a 1- and 3-h Infusion in a Phase I Study," Anti-Cancer Drugs, vol. 13, No. 4, pp. 381-393, Apr. 2002.

van Kesteren et al. "Yondelis® (trabectedin, ET-743): The Development of an Anticancer Agent of Marine Origin" Anti-Cancer Drugs, vol. 14, No. 7, pp. 487-502, Aug. 2003.

van Steeg, H et al., "Xeroderma pigmentosum and the role of UV-induced DNA damage in skin cancer," Mol. Med. Tod., 1999, 5, 86.

Villalona-Calero, M. et al., "A phase I and pharmacokinetic study of ET-743, a novel DNA minor groove binder of marine origin, administered as a 1-hour infusion daily x 5 days," Annals Oncology, Abstract 453, 1998.

Villalona-Calero, M. et al., "Final results of a Phase I and pharmacokinetic (PK) study of the marine minor groove binder ET-743 on a daily x 5 schedule," 1999 ASCO Annual Meeting Proceedings, Abstract No. 691, May 15-18, 1999.

(56) References Cited

OTHER PUBLICATIONS

Villalona-Calero et al., "A Phase I and Pharmacokinetic Study of Ecteinascidin-743 on a Daily x 5 Schedule in Patients with Solid Malignancies," Clinical Cancer Research, vol. 8, pp. 75-85, 2002.
Wakasugi, M. et al., "The Non-catalytic Function of XPG Protein during Dual Incision in Human Nucleotide Excision Repair," J. Biol. Chem. 1997, 272, 16030-16034.
Weiwei et al., "Potent antitumor activity of ET-743 against human soft tissue sarcoma cell lines," Proceedings of the 1999 AACR-NCI-EORTC International Conference, Clinical Cancer Research, vol. 5, Supplement, p. 3790s, Abstract 305, Nov. 16-19, 1999.
Wiesenthal, "Is one 'sensitive' drug better than another?" downloaded from internet website <<http://weisenthal.org/feedback.html>>, Feb. 4, 2002.
Wollina, "Multicenter study of pegylated liposomal doxorubicin in patients with cutaneous T-cell lymphoma," Cancer 2003, 1:98(5):993-1001, published online Jul. 24, 2003.
Working, Peter K. et al., "Reduction of the cardiotoxicity of doxorubicin in rabbits and dogs by encapsulation in long-circulating, pegylated liposomes," JPET, vol. 289, No. 2, pp. 1128-1133, 1999.
Wright et al., "Antitumor Tetrahydroisoquinonline Alkaloids from the Colonial Ascidian Ecteinascidia Turbinata", J. Org. Chem., vol. 55, pp. 4508-4512, 1990.
Yondelis Summary of Product Characteristics as authorised by EMA in 2007.
Zelek et al., "Preliminary results of phase II study of ecteinascidin (ET-743) with the 24 hour (H) continuous infusion (CI) q3week schedule in pretreated" Clinical Cancer Research, vol. 6, Supplement, Abstract 212, pp. 4508s-4509s, NCI-EORTC-AACR Symposium on New Drugs in Cancer Therapy, Nov. 7-10, 2000.
Zeltia Group Annual Report 2002.
Zeltia, Junta General de Accionistas 2003.
Zewail-Foote et al., "Ecteinascidin 743: A Minor Groove Alkylator that Bends DNA Toward the Major Groove," J. Med. Chem. 42, 2493-7, Jul. 15, 1999.
Zewail-Foote, M. et al., "The inefficiency of incisions of ecteinascidin 743-DNA adducts by the UvrABC nuclease and the unique structural feature of the DNA adducts can be used to explain the repair-dependent toxicities of this antitumor agent," Chemistry & Biology 2001, 8, 1033-1049.
Andya et al., "Mechanisms of Aggregate Formation and Carbohydrate Excipient Stabilization of Lyophilized Humanized Monoclonal Antibdoy Formulations", 2003, 5(2), pp. 1-11, AAPS PharmSci.
Carter et al., "Trabectedin, A Review of its Use in Soft Tissue Sarcoma and Ovarian Cancer," Drugs, 70(3), pp. 355-376, 2010.
Demetri et al., "Ecteinascidin (ET-743) Shows Promising Activity in Distinct Populations of Sarcoma Patients: Summary of U.S.-Based Phase II Trials," 2000, ASCO Online, retrieved from <<http:www.asco.org/prof/me/html/00abstracts/mel/pham_2177.htm>>, retrieved on Oct. 4, 2002.
Fung-Kee-Fung et al., "Optimal Chemotherapy Treatment for Women with Recurrent Ovarian Cancer," Current Oncology, 14(5):195-208, 2007.
Green et al., "Southwest Oncology Group Standard Response Criteria, Endpoint Definitions and Toxicity Criteria," Investigational New Drugs, 10:239- 253, 1992.
Garcia-Carbonero et al., "Ecteinascidin-743 (Et-743) for Chemotherapy-Naïve Patients with Advanced Soft Tissue Sarcomas: Multicenter Phase II and Pharmacokinetic Study," J. Clin. Oncol. 23:5484-5492, 2005.
Miller et al., "Reporting Results of Cancer Treatment," American Cancer Society, 47:207-214, 1981.
Rustin et al., "Use of CA-125 in Clinical Trial Evaluation of New Therapeutic Drugs for Ovarian Cancer," Clinical Cancer Research, 10:3919-3926, 2004.
Summons to Attend Oral Proceedings Pursuant to Rule 115(1) EPC for European Patent No. 1827500, Pharma Mar S.A., dated Oct. 6, 2011, 14 pages total.
Therasse et al., "New Guidelines to Evaluate the Response to Treatment in Solid Tumors," J. National Cancer Inst., 92(3):205-16, 2000.
Trosko et al., "Mechanism of up-regulated Gap Junctional Intercelluar Communication during Chemoprevention and Chemotherapy of Cancer," Mutation Research, 480-481, pp. 219-229, 2001.
Zeltia SA and Dependent Companies, Management Report, Annual Report, 1999.
Wirth et al., "Maillard Reaction of Lactose and Fluoxetine Hydrochloride, a Secondary Amine," Journal of Pharmacuetical Sciences, 87(1), pp. 31-39, Jan. 1998.
Notices of Opposition filed against EP Patent No. 1365808 by Teva Pharmaceutical Industries Ltd., Nov. 24, 2011.

\* cited by examiner

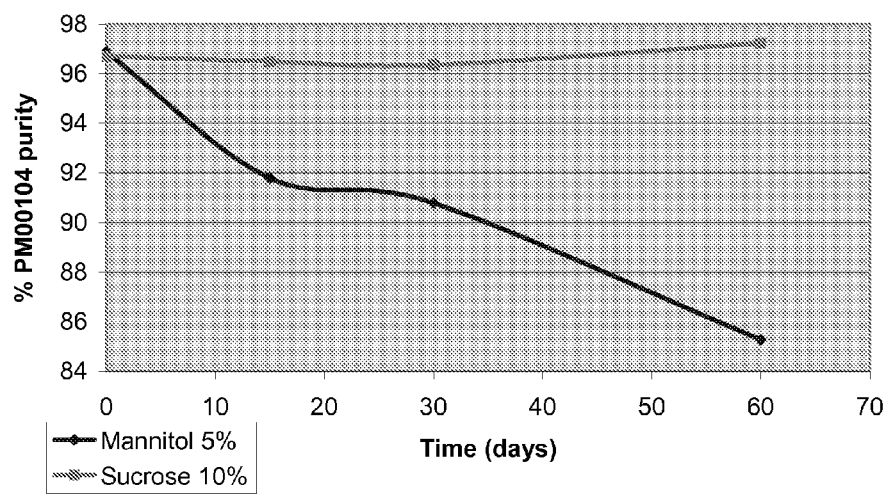

FORMULATIONS COMPRISING JORUMYCIN-, RENIERAMYCIN-, SAFRACIN- OR SAFRAMYCIN-RELATED COMPOUNDS FOR TREATING PROLIFERATIVE DISEASES

This application is the national phase entry under 35 U.S.C. §371 of PCT/GB2006/050362, filed Oct. 30, 2006, which claims priority under 35 U.S.C. §119(a)-(d) to GB 0522082.7, filed Oct. 31, 2005, the entire contents of which are hereby incorporated by reference.

The present invention relates to formulations. More particularly it relates to compositions and formulations of jorumycin-, renieramycin-, safracin- and saframycin-related compounds, such as compounds PM00104 and PM00121.

BACKGROUND OF THE INVENTION

Jorumycin is a natural compound isolated from the skin and from the mucus of the Pacific nudibranch *Jorunna funebris* (Fontana A., et al., Tetrahedron (2000), 56, 7305-8). In addition, the family of renieramycins is disclosed as being isolated from sponges and tunicates (James M. F. et al. J. Am. Chem. Soc. (1982), 104, 265-269; Oku N., et al. Journal Natural Products (2003), 66, 1136-9). Safracin and saframycin compounds are disclosed in Manzanares I., et al. Curr. Med. Chem. Anti-Cancer Agents (2001), 1, 257-276, as well as in WO 00/18233 and WO 01/87894.

Because of the detailed description provided in such references and citations therein, the structural characterizations of such compounds are not given again explicitly herein; any person of ordinary skill in this technology is capable of obtaining such information directly from the sources cited here and related sources. At least two of such compounds, PM00104 and PM00121 will be referred to specifically herein to illustrate features of this invention.

PM00104 and PM00121 are synthetic alkaloids related to jorumycin and renieramycins, and also to safracin and saframycin compounds. They show the following chemical structures:

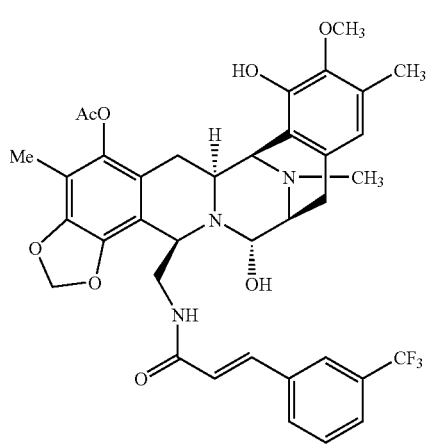

PM00104

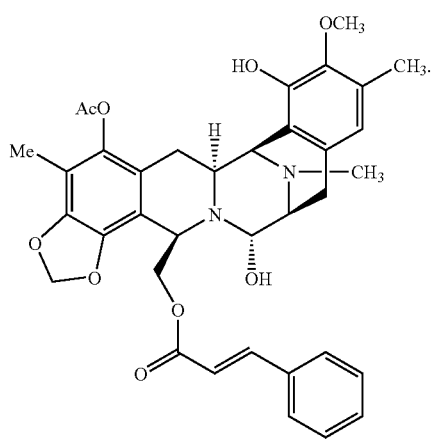

PM00121

A pharmaceutical composition comprising PM00104 or PM00121 together with a pharmaceutically acceptable carrier is claimed in WO 01/87894.

PM00104 has demonstrated a significant in vitro activity against solid and non-solid tumor cell lines as well as significant in vivo activity in several xenografted human cell lines in mice, such as breast and prostate. Preliminary insights into the mechanism of action of PM00104 suggested cell cycle changes, DNA binding properties and transcriptional inhibition. In addition, clinical phase I studies are currently ongoing with PM00104. For further activity data details of PM00104 and PM00121 see WO 01/87894

PM00104 and PM00121, as well as related compounds, are complex chemical entities, as revealed by their structural features. In addition, they exhibit limited aqueous solubility, and their stability, particularly in biocompatible forms and formulations, is difficult to predict and achieve. These characteristics challenge the ordinary skills and conventional methodologies in this technology, particularly when it comes to the preparation of formulations of these compounds that are to be readily used for medical purposes. Such uses preferably rely on formulations whose characteristics include one or more of the following: biocompatibility, stability under ambient conditions, or under conditions that are as near to ambient conditions as possible, with a shelf life that is as long as possible, and easy reconstitutability to form reconstituted solutions that are as stable under ambient, or near ambient conditions, for as long as possible.

In view of the potential of these compounds as antitumoral agents, there is a need to provide a formulation that can solve problems that conventional formulations and manufacturing methodologies do not address or do not completely solve. These problems include the problem of stability of these compounds. Embodiments of PM00104, PM00121 and related compounds formulations should preferably exhibit favourable freeze-drying properties, should preferably be susceptible of ready reconstitution, and they should preferably exhibit dilution properties, such as upon dilution with infusion fluid, while presenting as many of the desirable characteristics of formulations for medical use as referred to herein. As indicated above, embodiments of these formulations should be stable during long term storage. In addition, the formulation and its manufacturing methodology should satisfy biocompatibility standards and should thus allow for the effective use of a formulation vehicle that is non-toxic, at least at the concentrations used for infusion.

A general review of excipient-drug interactions in parental formulations is provided by Akers M. J., in Journal of Pharmaceutical Sciences, 91, 2002, 2283-2300. This reference provides, inter alia, a section on bulking agents and lyoprotectants, including this subject matter in the context of lyophilisation.

It is envisaged that the methodologies and formulations developed in the context of this invention are applicable to other related compounds, in addition to PM00104 and PM00121.

OBJECTS OF THE INVENTION

Specifically the invention relates to compositions and formulations of compounds of general formula (I):

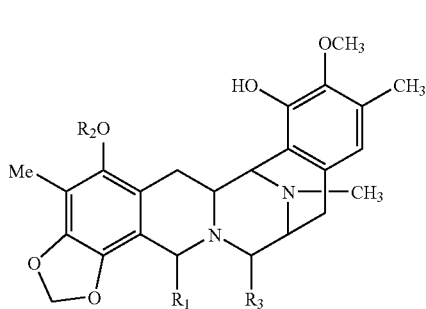

(I)

wherein $R_1$ is selected from the group consisting of —$CH_2$—$N(R_a)_2$ and —$CH_2$—$OR_a$, where each $R^a$ is independently selected from the group consisting of H, alkyl-CO—, haloalkyl-CO—, cycloalkylalkyl-CO—, haloalkyl-O—CO—, arylalkyl-CO—, arylalkenyl-CO—, heteroaryl-CO—, alkenyl-CO—, alkyl, alkenyl and amino acid acyl, or the two $R_a$ groups together with the N atom of —$CH_2$—N$(R_a)_2$ form a heterocyclic group;

$R_2$ is selected from alkyl-CO—, cycloalkyl-CO— and haloalkyl-CO—; and $R_3$ is OH or CN; or a pharmaceutically acceptable salt, derivative, prodrug or stereoisomer thereof. The various groups can be unsubstituted, or substituted.

Thus, the present invention provides stable formulations of compounds of general formula (I), and methods of making such formulations.

It is an object of this invention to provide a new stable formulation of compounds of general formula (I). In particular, a formulation is needed with great storage stability. In addition, there is especially a need to avoid the formation of impurities.

SUMMARY OF THE INVENTION

According to the present invention there are provided compositions which comprise a compound of general formula (I) and a disaccharide, and methods for preparing such compositions. Preferred embodiments of such compositions are of pharmaceutical purity.

Some embodiments of such compositions are provided by lyophilised formulations which comprise a compound of general formula (I) and a disaccharide. Methods for preparing such formulations are provided.

DETAILS OF THE INVENTION

We have found in the context of this invention that disaccharides stabilise formulations of compounds of general formula (I) as defined above.

In these compounds the substituents can be selected in accordance with the following guidance:

Alkyl groups preferably have from 1 to 12 carbon atoms. One more preferred class of alkyl groups has from 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Preferred alkenyl groups in the compounds of the present invention have one or more unsaturated linkages and from 2 to about 12 carbon atoms. One more preferred class of alkenyl groups has from 2 to about 6 carbon atoms, and most preferably 2, 3 or 4 carbon atoms. The term alkenyl as used herein refers to both cyclic and noncyclic groups.

Suitable aryl groups in the compounds of the present invention include single and multiple ring compounds, including multiple ring compounds that contain separate and/or fused aryl groups. Typical aryl groups contain from 1 to 3 separated or fused rings and from 6 to about 18 carbon ring atoms. Specially preferred aryl groups include substituted or unsubstituted phenyl, naphthyl, biphenyl, phenanthryl and anthracyl.

Suitable heterocyclic groups include heteroaromatic and heteroalicyclic groups. Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol groups. Suitable heteroalicyclic groups in the compounds of the present invention contain one, two or three heteroatoms selected from N, O or S atoms and include, e.g., tetrahydrofuranyl, tetrahydropyranyl, piperidinyl, morpholino and pyrrolindinyl groups. Phthalimido is another candidate heterocyclic group.

Suitable amino acid acyl groups include alanyl, arginyl, aspartyl, cystyl, glutamyl, glutaminyl, glycyl, histidyl, hydroxyprolyl, isoleucyl, leucyl, lysyl, methionyl, phenylalanyl, prolyl, seryl, threonyl, tyronyl, tryptophyl, tyrosyl, valyl, as well as other amino acid groups, which may be L- or D-.

The groups mentioned herein may be substituted at one or more available positions by one or more suitable groups such as R', OR', =O, SR', SOR', $SO_2R'$, $NO_2$, NHR', $N(R')_2$, =N—R', NHCOR', $N(COR')_2$, $NHSO_2R'$, CN, halogen, C(=O)R', $CO_2R'$, OC(=O)R', wherein each of the R' groups is independently selected from hydrogen, OH, $NO_2$, $NH_2$, SH, CN, halogen, =O, C(=O)H, C(=O)alkyl, $CO_2H$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl and substituted or unsubstituted aryl. Suitable halogen substituents in the compounds of the present invention include F, Cl, Br and I. Where such groups are themselves substituted, the substituents may be chosen from R", OR", =O, SR", SOR", $SO_2R"$, $NO_2$, NHR''',$(R")_2$ =N—R", NHCOR", N $(COR")_2$, $NHSO_2R"$, CN, halogen, C(=O)R", $CO_2R"$, OC(=O)R", wherein each of the R" groups is independently selected from the group consisting of hydrogen, OH, $NO_2$, $NH_2$, SH, CN, halogen, =O, C(=O)H, C(=O)

alkyl, CO$_2$H, unsubstituted C$_1$-C$_{12}$ alkyl, unsubstituted alkenyl, unsubstituted C$_2$-C$_{12}$ alkynyl and unsubstituted aryl.

The term "pharmaceutically acceptable salts, derivatives, prodrugs" refers to any pharmaceutically acceptable salt, ester, solvate, hydrate or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

The compounds of the invention may be in crystalline form either as free compounds or as solvates (e.g. hydrates) and it is intended that both forms are within the scope of the present invention. Methods of salvation are generally known within the art.

Any compound that is a prodrug of a compound of formula (I) is within the scope and spirit of the invention. The term "prodrug" is used in its broadest sense and encompasses those derivatives that are converted in vivo to the compounds of the invention. Such derivatives would readily occur to those skilled in the art, and include, for example, compounds where a free hydroxy group is converted into an ester derivative.

The compounds of the present invention represented by the above described formula (I) may include enantiomers depending on their asymmetry or diastereoisomers. Stereoisomerism about the double bond is also possible, therefore in some cases the molecule could exist as (E)-isomer or (Z)-isomer. The single isomers and mixtures of the isomers fall within the scope of the present invention.

Examples of compounds of the present invention include those disclosed for example in WO 00/18233 and WO 01/87894. We incorporate by specific reference each of the compounds identified in the respective examples of these PCT filings. More generally we incorporate by specific reference the content of these two PCT filings for their disclosure of compounds of present formula (I). We adopt the mention of preferred groups given in those texts, particularly as they apply to the present groups R$^1$ and R$^2$, especially R$^1$.

R$^3$ is usually OH.

Preferred compounds of this invention are those with the following chemical structure:

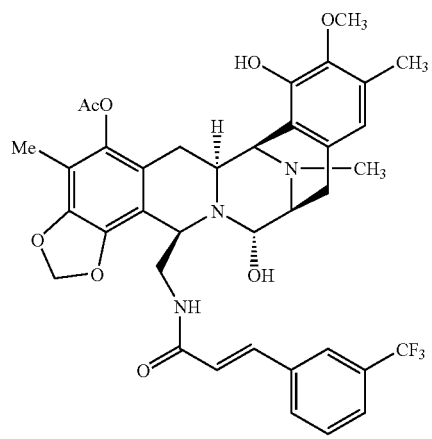

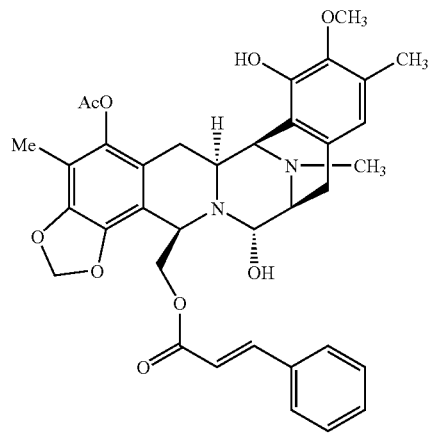

Compounds of general formula (I), including PM00104 and PM00121, are complex chemical entities whose behaviour in formulations is not predictable in terms of the behaviour of other unrelated chemical substances. Such behaviour is even more difficult to predict when at least one compound of general formula (I) is included as the active substance in a formulation that is to satisfy biocompatibility standards, including medical standards. We have further found in this regard that the use of disaccharides as bulking agents can drastically reduce the formation of impurities during the lyophilisation process and storage of PM00104 and PM00121 compositions.

In addition, the use of disaccharides also improves the storage conditions allowing long term storage of the lyophilised formulation in a wide temperature range, including refrigeration conditions and room temperature. The term "stable" as used herein in, for example the expression "a stable PM00104 or PM00121 formulation", refers to a formulation that satisfies stability characteristics as reported herein and equivalents thereof, that are not possessed by conventional formulations and that are not achieved when the formulation is prepared by conventional manufacturing methodologies.

Examples of embodiments of the present invention are provided by novel pharmaceutically acceptable compositions comprising a compound of general formula (I) and a disaccharide. Examples of suitable disaccharides include lactose, trehalose, sucrose, and combinations thereof. Additional examples of disaccharides that can be used in some embodiments of this invention include at least one of maltose, isomaltose, cellobiose, isosaccharose, isotrehalose, sorbose, turanose, melibiose, gentiobiose, and mixtures thereof. Sucrose is currently preferred. In other embodiments of the invention, the composition comprises a compound of general formula (I) and a lactose free disaccharide. In other embodiments of the invention, the composition comprises a compound of general formula (I) and a trehalose free disaccharide. In other embodiments of the invention, the composition comprises a compound of general formula (I) and a sucrose free disaccharide. In other embodiments of the invention, the composition comprises a compound of general formula (I) and a maltose free disaccharide. In other embodiments of the invention, the composition comprises a compound of general formula (I) and an isomaltose free disaccharide. In other embodiments of the invention, the composition comprises a compound of general formula (I) and a cellobiose free disaccharide. In other embodiments of the invention, the composition comprises a compound of general formula (I) and an isosaccharose free disaccharide. In other embodiments of the invention, the composition comprises a compound of general formula (I) and an isotrehalose free disaccharide. In other embodiments of the invention, the composition comprises a compound of general formula (I) and a sorbose free disaccharide. In other embodiments of the invention, the composition comprises a compound of general formula (I) and a turanose free disaccharide. In other embodiments of the invention, the composition comprises a compound of general formula (I) and a melibiose free disaccharide. In other embodiments of the invention, the composition comprises a compound of general formula (I) and a gentiobiose free disaccharide. Thus, in some embodiments, the composition of this invention contains less than 2% or less than 1% or less than 0.5% or less than 0.2% or less than 0.1% by weight of at least one of, preferably each of, lactose, trehalose, sucrose, maltose, isomaltose, cellobiose, isosaccharose, isotrehalose, sorbose, turanose, melibiose, and gentiobiose.

The terms "mixtures thereof" and "combinations thereof" as used herein refer to at least two entities that provide the antecedent basis for the terms "mixtures thereof" or "combinations thereof". By way of illustration, but not as a limitation, the terms "product comprising at least one of A, B, C, and mixtures thereof" refer to embodiments of the product for which any one of the following is satisfied: A is in the product; B is in the product; C is in the product; A and B are in the product; A and C are in the product; B and C are in the product; and A, B and C are in the product.

Furthermore, it is understood that terms such as "reacting", "forming", and related terms, applied to a chemical entity herein refer to any one of: (a) the chemical entity as such, and (b) the chemical entity in the form in which such entity is present in the reaction medium. Analogously, to name a chemical entity or to give its formula in the context of an operation or reaction step, or to name it or give its formula as being in a medium, whether solid or liquid, including products, formulations, and combinations, refers herein to any one of: (a) the entity as such, and (b) the entity in the form in which such entity is present in the medium. For example, naming an acidic chemical entity herein refers to whichever form or forms such entity is present in the context in which it is named. By way of illustration, but not as a limitation, naming the chemical entity "sodium chloride" or providing its chemical formula refers herein to the entity NaCl as such diatomic molecule, if such is the form in which sodium chloride is present in the relevant medium; it also refers to the collection of undissociated and/or dissociated chemical species if sodium chloride in the relevant medium is entirely or partially dissociated, including species in such medium that are solvated, part of cages, associated with other species, etc.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

The active substance or substances in the context of this invention can be of natural, semisynthetic or synthetic origin, including combinations of origins. In embodiments where the active substance is a compound such as PM00104 or PM00121, these compounds are of synthetic or semisynthetic origin and can be prepared following the disclosure of WO 01/87894, which is incorporated in full by reference.

The ratio of the active substance to the bulking agent in embodiments of this invention is determined according to the solubility of the bulking agent and, when the formulation is freeze dried, also according to the freeze-dryability of the bulking agent. It is envisaged that this ratio (w/w) can be about 1:1 in some embodiments, about 1:5 in other embodiments, about 1:10 in still other embodiments, while other embodiments illustrate ratios in the range from about 1:10 to about 1:1. It is envisaged that other embodiments have such ratios in the range from about 1:10 to about 1:80, and still further embodiments have such ratios in the range from about 1:80 to about 1:1500. When the active compound is PM00104 or PM00121, the ratio (w/w) of active ingredient to bulking agent is typically from about 1:80 to about 1:1500, preferably from about 1:100 to about 1:800, more preferably from about 1:100 to about 1:400, and even more preferably about 1:200.

The lyophilised material is usually presented in a vial which contains a specified amount of active compound. When the active compound is PM00104, active amounts are illustrated by 2.5 mg/vial. When the active compound is PM00121, active amounts are illustrated by 1 mg/vial.

The present invention is not limited by specific container forms or designs, as long as the container is acceptable for its intended use and standards therefore. Embodiments of this invention are provided with a formulation contained in vials.

The lyophilised formulations of this invention can be reconstituted and diluted to give a composition of this invention in the form of a solution ready for intravenous injection. The actual amounts of reconstituting fluid are not limiting features of embodiments of this invention. By way of illustrations, but not as limitations, embodiments of lyophilised formulations according to this invention are reconstituted with a volume of water. Most of such volumes do not exceed about 20 ml, with preferred volumes being in the range from about 1 ml to about 15 ml, more preferably in the range from about 1 ml to about 10 ml, and even more preferably in the range from about 3 ml to about 8 ml, and even more preferably about 5 ml. When the active substance is embodied by PM00104, the reconstituted solution in such embodiments contains a concentration of PM00104 up to 5 mg/ml, with concentrations of about 2.5 mg/ml, about 1 mg/ml, and about 0.5 mg/ml being preferred.

Reconstituted embodiments of the present invention can further be diluted if so desired, with this further dilution not being a limitation of the present invention. This further dilution is preferably carried out with an aqueous system which is usually 0.9% sodium chloride or 5% glucose. The reconstituted solution will be diluted depending on the concentration in the reconstituted solution and the desired concentration in the diluted solution.

Embodiments of formulations of compounds of formula (I) according to this invention can be used in the treatment of a variety of cancers. It is understood that "treatment" in this context refers to an action that leads to an amelioration of the cancer condition(s). Furthermore, embodiments of formulations according to this invention can be used in the trials with laboratory tissues, including but not limited to clinical trials, analytical trials, and modelling assays.

Embodiments of this invention that comprise compounds of formula (I) are preferably administered by infusion. The infusing step is typically repeated on a cyclic basis, which may be repeated as appropriate over for instance 1 to 20 cycles. The cycle includes a phase of infusing a formulation of a compound of formula (I), and usually also a phase of not infusing the active substance. Typically the cycle is worked out in weeks, and thus the cycle normally comprises one or more weeks of an active substance infusion phase, and one or more weeks to complete the cycle. We prefer that infusion times of up to 24 hours are used, more preferably 1-12 hours, with 1-6 hours most preferred. Short infusion times which allow treatment to be carried out without an overnight stay in hospital are especially desirable. However, infusion may be 12 to 24 hours or even longer if required.

Embodiments of formulations of this invention that contain a compound of formula (I) can be made by freeze-drying a composition of this invention in the form of a bulk solution including a compound of formula (I) and disaccharide. Usually the bulk solution will be buffered, for example to a pH of about 4. Suitable buffering agents include phosphate buffer, citrate buffer, phosphate/citrate buffer (a mixture of phosphate buffer and citrate buffer), lactate buffer, ascorbate buffer, tartaric/citrate buffer, bicarbonate/hydrochloric acid buffer, acetate buffer, succinate buffer and glycine/hydrochloric acid buffer. Mixtures of buffers can be used. Biocompatible buffers that permit the control of pH at a desired value provide additional embodiments of this invention.

Other components can be included in the bulk solution, for example surface-active agents such as polyoxyethylene sorbitan monooleate (also known as polysorbate) or polyoxyl 40 stearate. Other possible surface-active agents include phospholipids, such as a lecithin; polyoxyethylene-polyoxypropylene copolymers, such as a Pluronic surfactant; polyoxyethylene esters of 12-hydroxysteraric acid, such as a Solutol surfactant; ethoxylates of cholesterol, such as diacyl glycerol, dialkyl glycerol; bile salts, such as sodium cholate, sodium deoxycholate; sucrose esters, such as sucrose monolaurate, sucrose monooleate; polyvinyl pyrrolidone (PVP); or polyvinyl alcohol (PVA).

The formulation is normally supplied as a vial containing the lyophilised product. This supply form, however, is not a limitation of the present invention. To provide a vial containing the lyophilised product, the bulk solution is added to a vial and freeze-dried.

The freeze-drying is carried out in some embodiments of this invention by using reduced secondary drying times. A preferred protocol involves cooling to a temperature of about −40° C. to about −50° C., primary drying at 80 to 85 μbar for 25 to 50 hours, and secondary drying at a lower pressure and at above 0° C. for 3 to 20 hours.

Embodiments of this invention comprise lyophilization by cooling product below −40° C. The primary drying is performed at a temperature from about −20° C. to about −27° C. and a pressure of about 85 μbar for approximately 35 to 46 hours. The secondary drying is carried out at a temperature from about 20° C. to about 25° C. for approximately 30 to 45 hours.

Embodiments of formulations of this invention are suitable for storage at temperatures significantly higher than conventional formulation storage temperatures. Examples of storage temperatures for formulations according to this invention are around +5° C. These temperatures are readily provided by ordinary refrigerators.

DRAWING OF THE INVENTION

FIG. 1. Comparative PM00104% purity evolution of two PM00104 formulations, one comprising sucrose and the other one mannitol, stored at 40° C./70% RH during 3 months.

EXAMPLES

Example 1

This example discloses a comparative stability study of two PM00104 formulations, one using mannitol as bulking agent, and the other one using sucrose, which is a disaccharide and illustrates the present invention.

The composition of the bulk solution for each of the formulations was as follows (Table I):

TABLE I

| Component | Mannitol Formulation | Sucrose Formulation |
| --- | --- | --- |
| PM00104 | 0.1 mg/ml | 0.1 mg/ml |
| Mannitol | 5% | — |
| D-(+)-Sucrose | — | 100 mg/ml |
| Potassium dihydrogen phosphate | 6.8 mg/ml | 6.8 mg/ml |
| Phosphoric acid | q.s. to pH 4 | q.s. to pH 4 |
| Water for injection | — | q.s. to 1 ml |

Bulk solutions were prepared and freeze-dried by a standardised procedure.

Mannitol Formulation

A volume of 50 ml of mannitol formulation was prepared: 40 ml of a solution of potassium dihydrogen phosphate 0.05M (pH 4) was added to 5.493 mg of PM00104, and the mixture was maintained in agitation for 1 hour.

Then, 2.5 g of mannitol was added, washing the plate with 5 ml of a solution of phosphate buffer (pH 4). The mixture was stirred for one hour more. Following, the pH of the solution was adjusted to pH 4 with 1N phosphoric acid and the solution was brought to final weight of 52 g with phosphate buffer 0.05M (pH 4).

The solution was filtered through a PVDF filter and the filtered solution was filled into 10 ml glass vials at 2 ml/vial and vials were lyophilised according to the following procedure (Table II):

TABLE II

| Cycle | Step | Pressure | Setpoint T (° C.) | Slope (min) | Holding time |
| --- | --- | --- | --- | --- | --- |
| Loading | Shelves T$^a$ | | 5° C. | | |
| Freezing | Freeze 1 | | −45° C. | 0.5° C./min | 2 h 10 min |
| | Freeze 2 | | −45° C. | | 4 h |
| Vacuum | Ch vacuum | 0.5 mb | | | |

TABLE II-continued

| Cycle | Step | Pressure | Setpoint T (° C.) | Slope (min) | Holding time |
|---|---|---|---|---|---|
| Sublimation | 1° drying | 0.150 mb | −23° C. | 0.5° C./min | 2 h 30 min |
|  | 1° drying | 0.150 mb | −23° C. |  | 30 h |
| 2$^{nd}$ drying | 2° drying |  | 20° C. | 0.25° C./min | 3 h 30 min |
|  | 2° drying |  | 20° C. |  | 6 h |
|  | 2° drying |  | 25° C. |  | 30 min |
|  | 2° drying |  | 25° C. |  | 40 h |

After freeze-drying, the vials were sealed and were transferred to a refrigerated area (−20° C.).

Sucrose Formulation

A volume of 300 ml of sucrose formulation was prepared:

32.615 mg of PM00104 was added to 100 ml of a solution of potassium dihydrogen phosphate 0.05M (pH 4), washing the plate with additional 110 ml of the solution of potassium dihydrogen phosphate 0.05M (pH 4). Then, the mixture was maintained in agitation for 1 hour.

30 g of sucrose was added, washing the plate with 30 ml of solution of phosphate buffer (pH 4). The mixture was maintained in agitation for one hour more.

Following, the pH of the solution was adjusted to pH 4 with 1M phosphoric acid and the solution was brought to final weight of 300 g with water for injection.

The solution was filtered through a Millipore-Optiscale filter and the filtered solution was filled into 10 ml glass vials at 2 ml/vial and vials were lyophilised.

Stability testing was carried at a temperature of 5° C., 25° C./60% RH and 40° C./75% RH in the case of sucrose formulation and 40° C./75% RH in the case of mannitol formulation.

Table III and FIG. 1 show PM00104 chromatographic purity evolution of the formulations under study:

TABLE III

| | PM00104 purity (%) | | | |
|---|---|---|---|---|
| | 5° C. | 25° C./60% RH | 40° C./75% RH | |
| | Sucrose Formulation | Sucrose Formulation | Sucrose Formulation | Mannitol Formulation |
| t = 0 | 96.70% | 96.70% | 96.70% | 96.89% |
| t = 15 days | 96.85% | 96.44% | 96.50% | 91.79% |
| t = 1 month | 96.74% | 96.71% | 96.36% | 90.79% |
| t = 2 months | 97.23% | 97.10% | 97.24% | 85.26% |

Data in table III and FIG. 1 show that formulation containing sucrose displayed an improved stability at 40° C. and 75% RH with an insignificant purity decrease. This decrease is significantly lower than the decrease observed with the mannitol formulation.

Example 2

A PM00121 formulation comprising sucrose as bulking agent was prepared and its stability was evaluated at a temperature of 5° C., 25° C./60% RH and 40° C./75% RH.

For each vial the composition of the bulk solution was as follows (Table IV):

TABLE IV

| Component | mg/vial |
|---|---|
| PM00121 | 1 mg |
| Sucrose | 200 mg |
| Potassium dihydrogen phosphate | 13.6 mg |
| Polysorbate 80 | 0.2 mg |
| Phosphoric acid | q.s. to pH 4 |
| Water for injection | q.s. to 2 ml |

PM00121 formulation was prepared as follows:

100 ml of a solution of polysorbate 80 0.1% (pH 2.5) was added to 161.05 mg of PM00121, and subsequently additional 110 ml of solution of polysorbate 80 0.1% (pH 2.5) was also added. The mixture is maintained in agitation for 1 hour.

Then, 2.04 g of potassium dihydrogen phosphate was added, washing the plate with 15 ml of solution of polysorbate 80 0.1% (pH 2.5).

Following, 30 g of sucrose was weighed and added to the solution, washing the plate with 15 ml of solution of polysorbate 80 0.1% (pH 2.5). Then, the mixture is maintained in agitation for more than 1 hour.

Following, the pH of the solution was adjusted to pH 4 with 1M phosphoric acid and the solution was brought to final weight of 300 g with water for injection.

The solution was filtered with a Millipore-Optiscale filter. The filtered solution was filled into 10 ml glass vials at 2 ml/vial and maintained at −20° C. until the lyophilization process.

Lyophilization process was performed according to the following table V:

TABLE V

| Freezing time to −45° C.: | 150 min |
|---|---|
| Primary drying at 115 mTorr and −20° C. | 2300 min |
| Secondary drying at 75 mTorr and 25° C. | 600 min |

After freeze-drying, the vials were sealed and transferred to a refrigerated area (−20° C.).

Stability testing was carried at a temperature of 5° C., 25° C./60% RH and 40° C./75% RH.

Table VI discloses the PM00121 chromatographic purity of the formulation under study:

TABLE VI

| | PM00121 purity (%) | | |
|---|---|---|---|
| | 5° C. | 25° C./60% RH | 40° C./75% RH |
| t = 0 | 96.92% | 96.92% | 96.92% |
| t = 15 days | 97.83% | 97.63% | 97.38% |
| t = 1 month | 97.96% | 97.85% | 97.46% |
| t = 2 months | 97.98% | 97.12% | 95.71% |

It was noted that the formulation comprising the disaccharide was stable at 5° C. and 25° C./60% RH.

Example 3

Two PM00104 formulations, 104-F A and 104-F B, comprising sucrose as bulking agent were prepared and its stability was evaluated at a temperature of −20° C., 5° C., 25° C./60% RH and 45° C./75% RH.

For each formulation the composition of the bulk solution for each vial was as follows (Table VII):

TABLE VII

| Component | mg/vial |
|---|---|
| PM00104 | 2.5 mg |
| D-(+)-Sucrose | 500 mg |
| Potassium dihydrogen phosphate | 34 mg |
| Phosphoric acid | q.s to pH 4 |
| Water for injection | q.s to 5 ml |

Bulk solutions were prepared and freeze-dried using the following particular protocols:

Formulation 104-F A 1.750 l of bulk solution was prepared as follows:

153.125 ml of phosphoric acid 0.05N was added to 905.61 mg of PM00104. The mixture was stirred for 15 minutes. Then 1400 ml of water for injection was added, followed by the addition of 11.9 g of potassium dihydrogen phosphate and 175 g of sucrose. The mixture was maintained again in agitation for 1 h 15 min.

The pH of the solution was not needed to be adjusted to 3.8≤pH≤4, since its pH value was 3.91. The solution was brought to final weight of 1820 g with water for injection.

Then, the solution was filtered through a 0.22 μm Millipack®-20 filter. And the filtered solution was filled into 25 ml vials at 5.4 ml of bulk solution/vial and maintained at −20° C. until the lyophilization process.

Lyophilization process was performed according to the following table VIII:

TABLE VIII

| Cycle | Step | Pressure | Setpoint T (° C.) | Slope (min) | Holding time |
|---|---|---|---|---|---|
| Loading | Shelves T$^a$ | | −5° C. | | 10 min |
| Freezing | Freeze 1 | | −50° C. | 0.5° C./min | 1 h 50 min |
| | Freeze 2 | | −50° C. | | 3 h |
| Vacuum | Ch vacuum | 0.5 mb | | | |
| Sublimation | 1° drying | 0.080 mb | −27° C. | 0.5° C./min | 45 min |
| | 1° drying | 0.080 mb | −27° C. | | 45 h |
| 2$^{nd}$ drying | 2° drying | | 25° C. | 0.25° C./min | 3 h 30 min |
| | 2° drying | | 25° C. | | 40 h |
| | stoppering | | 25° C. | | |

The vials were sealed and transferred to a refrigerated area (−20° C.).

Formulation 104-F B 2.271 g of PM00104 was added to 100 ml of phosphoric acid 0.05N, washing the plate with 265 ml of phosphoric acid 0.05N. The mixture was stirred for 15 minutes. Then 3360 ml of water for injection was added, followed by the addition of 28.56 g of potassium dihydrogen phosphate. The mixture was stirred for 3 minutes and 420 g of sucrose was added. The mixture was maintained again in agitation for 1 h 15 min.

The pH of the solution was not needed to be adjusted to 3.8≤pH≤4, since its pH value was 3.84. The solution was brought to final weight of 4369 g with water for injection.

Then, the solution was filtered through a 0.22 μm filter. And the filtered solution was filled into 25 ml vials at 5 ml of bulk solution/vial and maintained at −20° C. until the lyophilization process.

Lyophilization process was performed according to the following table IX:

TABLE IX

| Cycle | Step | Pressure | Setpoint T (° C.) | Slope (min) | Holding time |
|---|---|---|---|---|---|
| Loading | Shelves T$^a$ | | −5° C. | | 80 min |
| Freezing | Freeze 1 | | −40° C. | 0.5° C./min | 1 h 50 min |
| | Freeze 2 | | −40° C. | | 3 h |
| Vacuum | Ch vacuum | 0.4 mb | | | |
| Sublimation | 1° drying | 0.085 mb | −27° C. | 0.5° C./min | 45 min |
| | 1° drying | 0.085 mb | −27° C. | | 35 h |
| 2$^{nd}$ drying | 2° drying | | 25° C. | 0.25° C./min | 3 h 30 min |
| | 2° drying | | 25° C. | | 30 h |
| | stoppering | | 25° C. | | |

After freeze-drying, the vials were sealed and were transferred to a refrigerated area (−20° C.).

Stability testing was carried with both formulations at a temperature of −20° C.±5° C., 5° C.±3° C., 25° C.±2° C./60% RH±5% RH and 40° C.±2° C./75% RH±5% RH.

Table X shows the PM00104 chromatographic purity evolution of the formulation 104-FA during storage at −20° C., 5° C., 25° C./60% RH and 40° C./70% RH.

TABLE X

| | PM00104 purity (%) | | | |
|---|---|---|---|---|
| | −20° C. | 5° C. | 25° C./60% RH | 40° C./75% RH |
| t = 0 | 98.24% | 98.24% | 98.24% | 98.24% |
| t = 1 month | — | — | — | 98.13% |
| t = 2 months | — | — | 98.26% | 98.16% |
| t = 3 months | — | 97.97% | 98.11% | 97.98% |
| t = 6 months | 98.13% | 98.09% | 98.09% | — |
| t = 9 months | — | 98.07% | — | — |
| t = 12 months | 98.02% | 97.99% | — | — |

Table XI shows the PM00104 chromatographic purity evolution of the formulation 104-FB during storage at −20° C., 5° C., 25° C./60% RH and 40° C./70% RH.

TABLE XI

| | PM00104 purity (%) | | | |
|---|---|---|---|---|
| | −20° C. | 5° C. | 25° C./60% RH | 40° C./75% RH |
| t = 0 | 98.54% | 98.54% | 98.54% | 98.54% |
| t = 1 month | — | — | — | 98.20% |
| t = 2 months | — | — | — | 98.01% |
| t = 3 months | — | 98.44% | 98.37% | 97.78% |
| t = 6 months | 98.37% | 98.33% | 98.25% | 96.78% |
| t = 9 months | — | 98.19% | 98.15% | — |
| t = 12 months | 97.91% | 97.91% | 97.55% | — |
| t = 18 months | 98.22% | 98.15% | 98.12% | — |
| t = 24 months | 98.32% | 98.29% | 97.77% | — |

Data in tables X and XI show that the purity evolution of formulations stored 5° C. and 25° C./60% RH is comparable to those of formulation stored at −20° C. Therefore no major degradation is found at 5° C. and 25° C./60% RH showing that formulations comprising a disaccharide can be in storage at least at +5° C. during a long period of time.

All the references cited herein are incorporated by reference in their entirety. The features and advantages of this invention are apparent in light of the disclosure provided herein. Based on this disclosure, modifications and adaptations to various conditions and usages can be made, thus generating embodiments within the scope of this invention.

The invention claimed is:

1. A pharmaceutical composition comprising a disaccharide and a compound of general formula (I):

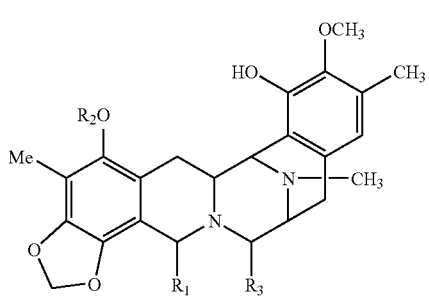

(I)

wherein $R_1$ is selected from the group consisting of —$CH_2$—$N(R^a)_2$ and —$CH_2$—$OR^a$, where each $R^a$ is independently selected from the group consisting of H, alkyl-CO—, haloalkyl-CO—, cycloalkylalkyl-CO—, haloalkyl-O—CO—, arylalkyl-CO—, arylalkenyl-CO—, heteroaryl-CO—, alkenyl-CO—, alkyl, alkenyl and amino acid acyl, or the two $R^a$ groups together with the N atom of —$CH_2$—$N(R^a)_2$ form a heterocyclic group;

$R_2$ is selected from alkyl-CO—, cycloalkyl-CO— and haloalkyl-CO—; and $R_3$ is OH or CN; or a pharmaceutically acceptable salt or stereoisomer thereof; and wherein said $R_1$ and $R_2$ independently, are unsubstituted or substituted at one or more available positions by one or more groups selected from R', OR', =O, SR', SOR', $SO_2$R', $NO_2$, NHR', $N(R')_2$, =N—R', NHCOR', $N(COR')_2$, $NHSO_2$R', CN, halogen, C(=O)R', $CO_2$R', OC(=O)R', wherein each of the R' groups is independently selected from the group consisting of hydrogen, OH, $NO_2$, $NH_2$, SH, CN, halogen, =O, C(=O) H, C(=O)alkyl, $CO_2$H, substituted or unsubstituted $C_1$-$C_{12}$ alkyl, substituted or unsubstituted $C_2$-$C_{12}$ alkenyl, substituted or unsubstituted $C_2$-$C_{12}$ alkynyl and substituted or unsubstituted aryl, where, when such R' groups are themselves substituted, the substituents of R' are independently selected from the group consisting of R'', OR'', =O, SR'', SOR'', $SO_2$R'', $NO_2$, NHR'', $N(R'')_2$, =N—R'', NHCOR'', $N(COR'')_2$, $NHSO_2$R'', CN, halogen, C(=O)R'', $CO_2$R'', OC(=O)R'', wherein each R'' groups is independently selected from the group consisting of hydrogen, OH, $NO_2$, $NH_2$, SH, CN, halogen, =O, C(=O) H, C(=O)alkyl, $CO_2$H, unsubstituted $C_1$-$C_{12}$ alkyl, unsubstituted $C_2$-$C_{12}$ alkenyl, unsubstituted $C_2$-$C_{12}$ alkynyl and unsubstituted aryl.

2. A composition according to claim 1, wherein said compound is the compound of formula (II) (PM00104) or formula (III) (PM00121):

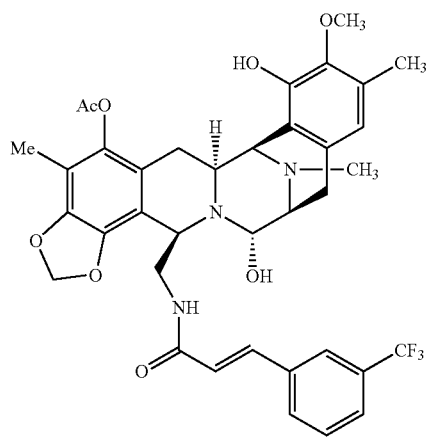

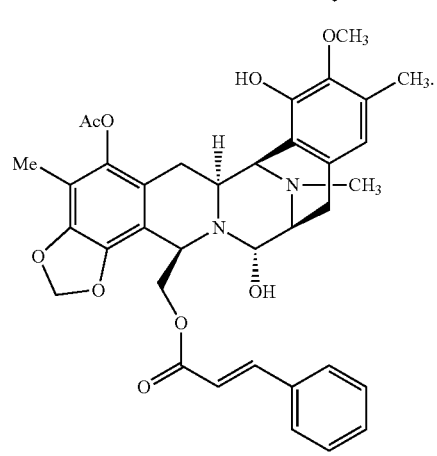

3. A composition according to claim 1, wherein said disaccharide is selected from the group consisting of lactose, trehalose, sucrose, and mixtures thereof.

4. A composition according to claim 3, wherein said disaccharide is sucrose.

5. A composition according to claim 1, wherein the ratio (w/w) of compound to disaccharide is from about 1:80 to about 1:1500.

6. A composition according to claim 5, wherein the ratio (w/w) of compound to disaccharide is from about 1:100 to about 1:400.

7. A composition according to claim 6, wherein the ratio (w/w) of compound to disaccharide is about 1:200.

8. A composition according to claim 1, which further comprises a buffering agent.

9. A composition according to claim 8, wherein said buffering agent is a phosphate buffer.

10. A composition according to claim 1 which further comprises a surface-active agent.

11. A composition according to claim 10, wherein the surface-active agent is a polyoxyethylene sorbitan monooleate.

12. A composition according to claim 1, wherein the composition is in the form of a lyophilised formulation.

13. A composition according to claim 1, wherein the composition is in the form of a lyophilised formulation.

14. A composition according to claim 13, wherein said PM00104 is in present in said composition an amount of about 2.5 mg.

15. A composition according to claim 14, wherein said disaccharide is sucrose, wherein said sucrose is present in said composition in an amount of about 500 mg and wherein said formulation further comprises about 34 mg phosphate, wherein said 34 mg phosphate is calculated as potassium dihydrogen phosphate.

16. A composition according to claim 3, wherein said disaccharide is selected from the group consisting of lactose, trehalose, sucrose, and mixtures thereof.

17. A composition according to claim 16, wherein said disaccharide is sucrose.

18. A composition according to claim 3, wherein the ratio (w/w) of compound to disaccharide is from about 1:80 to about 1:1500.

19. A composition according to claim 18, wherein the ratio (w/w) of compound to disaccharide is from about 1:100 to about 1:400.

20. A composition according to claim 19, wherein the ratio (w/w) of compound to disaccharide is about 1:200.

21. A composition according to claim 3, which further comprises a buffering agent.

22. A composition according to claim 21, wherein said buffering agent is a phosphate buffer.

23. A composition according to claim 3 which further comprises a surface-active agent.

24. A composition according to claim 23, wherein the surface-active agent is a polyoxyethylene sorbitan monooleate.

25. A composition according to claim 3, wherein said composition does not include a surface-active agent.

26. A pharmaceutical composition comprising a disaccharide and a compound of general formula (I):

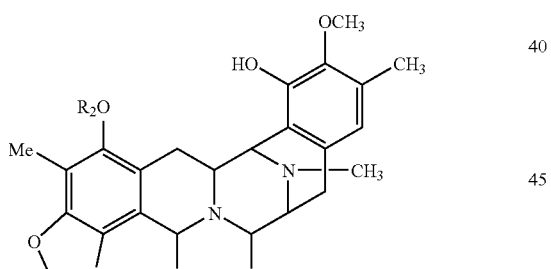

(I)

wherein $R_1$ is selected from the group consisting of —$CH_2$—$N(R^a)_2$ and —$CH_2$—$OR^a$, where each $R^a$ is independently selected from the group consisting of H, alkyl-CO—, haloalkyl-CO—, cycloalkylalkyl-CO—, haloalkyl-O—CO—, arylalkyl-CO—, arylalkenyl-CO—, heteroaryl-CO—, alkenyl-CO—, alkyl, alkenyl and amino acid acyl, or the two $R^a$ groups together with the N atom of —$CH_2$—$N(R^a)_2$ form a heterocyclic group;

$R_2$ is selected from alkyl-CO—, cycloalkyl-CO— and haloalkyl-CO—; and $R_3$ is OH or CN; or a pharmaceutically acceptable salt or stereoisomer thereof.

27. A pharmaceutical composition comprising a disaccharide and a single active anti-tumor agent selected from compounds of general formula (I):

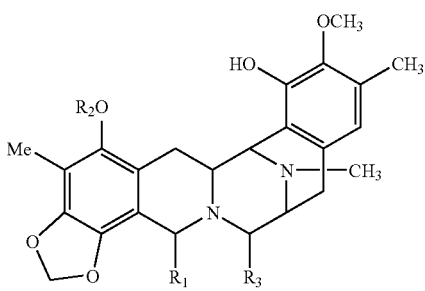

(I)

wherein $R_1$ is selected from the group consisting of —$CH_2$—$N(R^a)_2$ and —$CH_2$—$OR^a$, where each $R^a$ is independently selected from the group consisting of H, alkyl-CO—, haloalkyl-CO—, cycloalkylalkyl-CO—, haloalkyl-O—CO—, arylalkyl-CO—, arylalkenyl-CO—, heteroaryl-CO—, alkenyl-CO—, alkyl, alkenyl and amino acid acyl, or the two $R^a$ groups together with the N atom of —$CH_2$—$N(R^a)_2$ form a heterocyclic group;

$R_2$ is selected from alkyl-CO—, cycloalkyl-CO— and haloalkyl-CO—; and $R_3$ is OH or CN; or a pharmaceutically acceptable salt or stereoisomer thereof; and wherein said $R_1$ and $R_2$ independently, are unsubstituted or substituted at one or more available positions by one or more groups selected from R', OR', =O, SR', SOR', $SO_2$R', $NO_2$, NHR', $N(R')_2$, =N—R', NHCOR', $N(COR')_2$, $NHSO_2$R', CN, halogen, C(=O)R', $CO_2$R', OC(=O)R', wherein each of the R' groups is independently selected from the group consisting of hydrogen, OH, $NO_2$, $NH_2$, SH, CN, halogen, =O, C(=O)H, C(=O)alkyl, $CO_2$H, substituted or unsubstituted $C_1$-$C_{12}$ alkyl, substituted or unsubstituted $C_2$-$C_{12}$ alkenyl, substituted or unsubstituted $C_2$-$C_{12}$ alkynyl and substituted or unsubstituted aryl, where, when such R' groups are themselves substituted, the substituents of R' are independently selected from the group consisting of R", OR", =O, SR", SOR", $SO_2$R", $NO_2$, NHR", $N(R")_2$, =N—R", NHCOR", $N(COR")_2$, $NHSO_2$R", CN, halogen, C(=O)R", $CO_2$R", OC(=O)R", wherein each R" groups is independently selected from the group consisting of hydrogen, OH, $NO_2$, $NH_2$, SH, CN, halogen, =O, C(=O)H, C(=O)alkyl, $CO_2$H, unsubstituted $C_1$-$C_{12}$ alkyl, unsubstituted $C_2$-$C_{12}$ alkenyl, unsubstituted $C_2$-$C_{12}$ alkynyl and unsubstituted aryl.

28. The composition according to claim 1, wherein said composition has improved stability compared to a formulation using mannitol instead of the disaccharide.

29. The composition according to claim 2, wherein said composition has improved stability compared to a formulation using mannitol instead of the disaccharide.

30. The composition according to claim 1, wherein said disaccharide is present in an amount sufficient to inhibit degradation of the anti-tumor agent after storage at 5° C. for 1 month compared to the same composition comprising mannitol instead of the disaccharide.

31. The composition according to claim 1, wherein said disaccharide is present in an amount sufficient to inhibit degradation of the anti-tumor agent after storage at 25° C. for 1 month compared to a composition comprising mannitol instead of the disaccharide.

32. The composition according to claim 1, wherein said disaccharide is present in an amount sufficient to inhibit degradation of the anti-tumor agent after storage of at 40° C. for 1 month compared to a composition comprising mannitol instead of the disaccharide.

33. A method of making a lyophilised formulation according to claim 12, comprising freeze-drying a bulk solution that comprises said compound and said disaccharide.

34. A method according to claim 33, wherein the compound is the compound of formula (II) (PM00104):

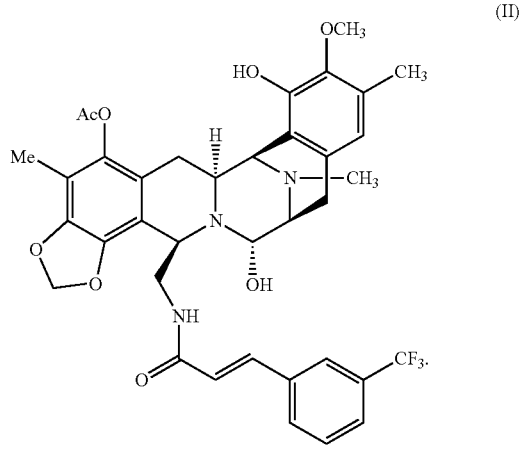 [SMILES: COc1c(C)cc2c(c1O)[C@@H]1[C@@H]3Cc4c(OC(C)=O)c(C)c5c(c4[C@H](CNC(=O)/C=C/c4cccc(C(F)(F)F)c4)N3[C@@H](O)[C@H](C2)N1C)OCO5]

35. A method of reducing the formation of impurities in said lyophilised formulation according to claim 12, comprising freeze-drying a bulk solution that comprises said compound and said disaccharide.

36. A method according to claim 35, wherein the compound is the compound of formula (II) (PM00104):

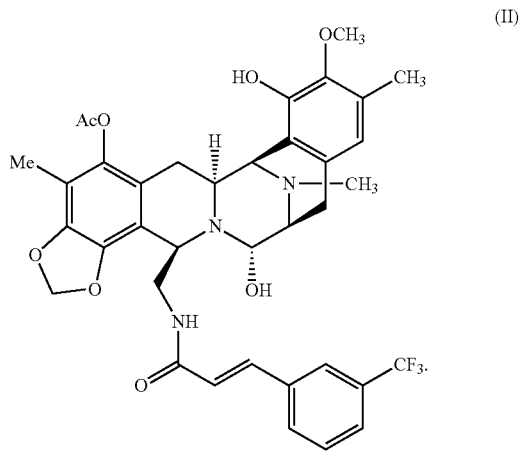 [SMILES: COc1c(C)cc2c(c1O)[C@@H]1[C@@H]3Cc4c(OC(C)=O)c(C)c5c(c4[C@H](CNC(=O)/C=C/c4cccc(C(F)(F)F)c4)N3[C@@H](O)[C@H](C2)N1C)OCO5]

37. A method of preparing a solution for intravenous infusion, comprising: providing a lyophilised formulation according to claim 12, adding water to form a reconstituted solution, and diluting said reconstituted solution with an aqueous system.

38. A method according to claim 37, wherein the compound is the compound of formula (II) (PM00104):

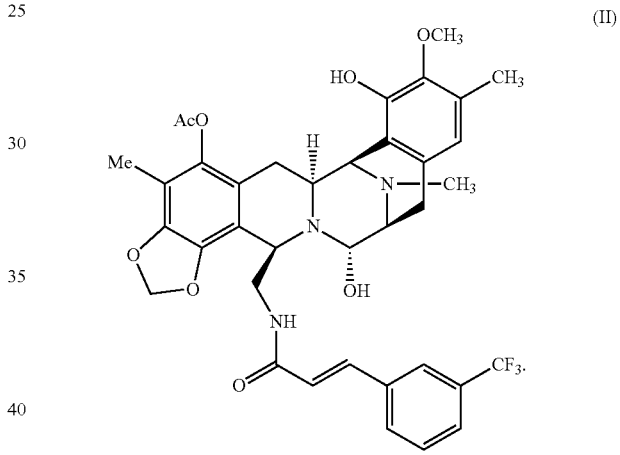

39. A method of treating cancer, which comprises intravenous infusion of a solution prepared by a method according to claim 37 or 38.

* * * * *